US008333974B2

(12) United States Patent
Weiss et al.

(10) Patent No.: US 8,333,974 B2
(45) Date of Patent: *Dec. 18, 2012

(54) CONTINUOUS DOSING REGIMENS FOR NEURAL STEM CELL PROLIFERATING AGENTS AND NEURAL STEM CELL DIFFERENTIATING AGENTS

(75) Inventors: Samuel Weiss, Calgary (CA); Christopher Gregg, Cambridge, MA (US); Allen Davidoff, Calgary (CA); Joseph Tucker, Calgary (CA)

(73) Assignee: Stem Cell Therapeutics Corp. (CA)

( * ) Notice: Subject to any disclaimer, the term of this patent is extended or adjusted under 35 U.S.C. 154(b) by 341 days.

This patent is subject to a terminal disclaimer.

(21) Appl. No.: 12/293,408

(22) PCT Filed: Mar. 16, 2007

(86) PCT No.: PCT/CA2007/000427
§ 371 (c)(1),
(2), (4) Date: Sep. 17, 2008

(87) PCT Pub. No.: WO2007/106987
PCT Pub. Date: Sep. 27, 2007

(65) Prior Publication Data
US 2009/0081205 A1    Mar. 26, 2009

Related U.S. Application Data

(60) Provisional application No. 60/783,500, filed on Mar. 17, 2006, provisional application No. 60/789,132, filed on Apr. 5, 2006, provisional application No. 60/862,669, filed on Oct. 24, 2006.

(51) Int. Cl.
*A61K 38/18* (2006.01)
*C07K 14/59* (2006.01)
*A61P 25/00* (2006.01)

(52) U.S. Cl. ........ 424/198.1; 514/7.6; 514/8.3; 514/9.7; 514/17.7; 514/18.2

(58) Field of Classification Search .................. None
See application file for complete search history.

(56) References Cited

U.S. PATENT DOCUMENTS

| 4,703,008 A | 10/1987 | Lin |
| 4,767,628 A | 8/1988 | Hutchinson |
| 4,801,575 A | 1/1989 | Pardridge |
| 4,902,680 A | 2/1990 | Aroonsakul |
| 5,023,252 A | 6/1991 | Hseih |
| 5,128,242 A | 7/1992 | Arimura et al. |
| 5,198,542 A | 3/1993 | Onda et al. |
| 5,208,320 A | 5/1993 | Kitada et al. |
| 5,231,178 A | 7/1993 | Holtz et al. |
| 5,268,164 A | 12/1993 | Kozarich et al. |
| 5,326,860 A | 7/1994 | Onda et al. |
| 5,441,868 A | 8/1995 | Lin |
| 5,473,054 A | 12/1995 | Jameson et al. |
| 5,505,206 A | 4/1996 | Walloch |
| 5,506,107 A | 4/1996 | Cunningham et al. |
| 5,506,206 A | 4/1996 | Kozarich et al. |
| 5,521,069 A | 5/1996 | Onda et al. |
| 5,527,527 A | 6/1996 | Friden |
| 5,547,935 A | 8/1996 | Mullenbach et al. |
| 5,547,993 A | 8/1996 | Miki |
| 5,559,143 A | 9/1996 | McDonald et al. |
| 5,614,184 A | 3/1997 | Sytkowski et al. |
| 5,621,080 A | 4/1997 | Lin |
| 5,623,050 A | 4/1997 | Kitada et al. |
| 5,686,416 A | 11/1997 | Kozarich et al. |
| 5,723,115 A | 3/1998 | Serrero |
| 5,750,376 A | 5/1998 | Weiss et al. |
| 5,753,506 A | 5/1998 | Johe |
| 5,767,251 A * | 6/1998 | Reddy et al. ............... 530/397 |
| 5,773,569 A | 6/1998 | Wrighton et al. |
| 5,795,790 A | 8/1998 | Schinstine et al. |
| 5,801,147 A | 9/1998 | Kitada et al. |
| 5,833,988 A | 11/1998 | Friden |
| 5,837,460 A | 11/1998 | Von Feldt et al. |
| 5,851,832 A | 12/1998 | Weiss et al. |
| 5,877,169 A | 3/1999 | Simpkins |
| 5,885,574 A | 3/1999 | Elliott |
| 5,955,346 A | 9/1999 | Wells et al. |
| 5,977,307 A | 11/1999 | Friden et al. |
| 5,980,885 A | 11/1999 | Weiss et al. |
| 6,015,555 A | 1/2000 | Friden |
| 6,017,533 A | 1/2000 | Moro et al. |
| 6,048,971 A | 4/2000 | Sytkowski et al. |

(Continued)

FOREIGN PATENT DOCUMENTS

CA    2175992    5/1995

(Continued)

OTHER PUBLICATIONS

Wehmann et al., J. Clin. Invest., 68:184-194, Jul. 1981.*
Choi et al., Endocrinology, 140(11):5126-5135, 1999.*
Taoufik et al., Current Pharm Design, 14(33): 3565-3573, 2008.*
Molina-Holgado et al., J Neurochem, 114(5):1277-1290, Sep. 2010.*
Greenway et al., West Med J., 127(6):461-463, 1977.*
Arvidsson et al., Nature Medicine, 8:963-970, 2002.*
Horky et al., Journal of Comparative Neurology, 498(4):525-538, 2006.*
Jaigobin et al., Stroke and Pregnancy, Stroke 31:2948-2951, 2000.*
Lindvall and Kokala, Stroke 42:2369-2375, 2011.*

(Continued)

*Primary Examiner* — Daniel E Kolker
*Assistant Examiner* — Stacey MacFarlane
(74) *Attorney, Agent, or Firm* — Meunier Carlin & Curfman, LLC

(57) ABSTRACT

The present invention provides effective dosing regimes for neural stem cell proliferating agents, kits containing effective dosing regimes for neural stem cell proliferating agents, and uses thereof. In particular, neural stem cell proliferating agents, such as hCG, prolactin and EPO are delivered to mammalian subjects at low doses in a continuous fashion over several days, as opposed to delivery of high doses in a short period of time.

13 Claims, 6 Drawing Sheets

U.S. PATENT DOCUMENTS

| | | | |
|---|---|---|---|
| 6,165,783 | A | 12/2000 | Weiss et al. |
| 6,191,106 | B1 | 2/2001 | Mullenbach et al. |
| 6,239,105 | B1 | 5/2001 | Brewitt |
| 6,242,563 | B1 | 6/2001 | Dong |
| 6,294,346 | B1 | 9/2001 | Weiss et al. |
| 6,329,508 | B1 | 12/2001 | Friden |
| 6,333,031 | B1 | 12/2001 | Olsson et al. |
| 6,376,218 | B1 | 4/2002 | Hsu et al. |
| 6,395,546 | B1 | 5/2002 | Zobel et al. |
| 6,399,316 | B1 | 6/2002 | Onda et al. |
| 6,413,952 | B1 | 7/2002 | Luengo et al. |
| 6,429,186 | B1 | 8/2002 | Fuh et al. |
| 6,551,618 | B2 | 4/2003 | Baird et al. |
| 6,583,109 | B1 | 6/2003 | Gallo et al. |
| 6,618,698 | B1 | 9/2003 | Beausoleil et al. |
| 6,680,295 | B1 | 1/2004 | Arimura |
| 6,797,264 | B1 | 9/2004 | Eriksson |
| 6,812,027 | B2 | 11/2004 | Goldman et al. |
| 7,048,934 | B2 | 5/2006 | Thompson et al. |
| 7,132,287 | B2 | 11/2006 | Rajan et al. |
| 7,514,072 | B1 | 4/2009 | Ehrenreich et al. |
| 2002/0098178 | A1 | 7/2002 | Brand |
| 2003/0032181 | A1 | 2/2003 | Weiss et al. |
| 2003/0049838 | A1 | 3/2003 | Thompson et al. |
| 2003/0054549 | A1 | 3/2003 | Takebe et al. |
| 2003/0054551 | A1 | 3/2003 | Shingo et al. |
| 2003/0054998 | A1 | 3/2003 | Shingo et al. |
| 2003/0130197 | A1 | 7/2003 | Smith-Swintosky et al. |
| 2004/0038888 | A1 | 2/2004 | Mercer et al. |
| 2004/0092448 | A1 | 5/2004 | Ohta et al. |
| 2004/0209000 | A1 | 10/2004 | Curtiss et al. |
| 2005/0009847 | A1 | 1/2005 | Bertilsson et al. |
| 2005/0024543 | A1 | 2/2005 | Ramaswamy et al. |
| 2006/0089309 | A1 | 4/2006 | Tucker |
| 2006/0121007 | A1 | 6/2006 | Thompson et al. |
| 2006/0148084 | A1 | 7/2006 | Shingo et al. |
| 2007/0098698 | A1 | 5/2007 | Gregg et al. |
| 2007/0111932 | A1 | 5/2007 | Anderson |
| 2007/0179092 | A1 | 8/2007 | Ohta et al. |
| 2008/0286234 | A1 | 11/2008 | Eyink |
| 2009/0325289 | A1 | 12/2009 | Hatzfeld et al. |
| 2010/0028361 | A1 | 2/2010 | Smith et al. |
| 2010/0047233 | A1 | 2/2010 | Smith et al. |

FOREIGN PATENT DOCUMENTS

| | | |
|---|---|---|
| CA | 2353553 | 6/2000 |
| CA | 2556266 | 8/2005 |
| EP | 0467279 A3 | 1/1992 |
| WO | WO 90 05185 | 5/1990 |
| WO | WO 93 01275 | 1/1993 |
| WO | WO 94 09119 | 4/1994 |
| WO | WO 94 10292 | 5/1994 |
| WO | WO 96 09318 | 3/1996 |
| WO | WO9615226 | 5/1996 |
| WO | WO 96 40231 | 12/1996 |
| WO | WO 97 48729 | 12/1997 |
| WO | 9805353 | 2/1998 |
| WO | WO 99 15191 | 4/1999 |
| WO | WO 99 21966 | 5/1999 |
| WO | WO 99 51272 | 10/1999 |
| WO | WO 00 05260 | 2/2000 |
| WO | WO 00 13650 | 3/2000 |
| WO | WO 00 30675 | 6/2000 |
| WO | WO 01 28574 | 4/2001 |
| WO | WO0159074 | 8/2001 |
| WO | WO 03 018782 | 3/2003 |
| WO | WO 03 024472 | 3/2003 |
| WO | WO 03 040310 | 5/2003 |
| WO | WO 03 092716 | 11/2003 |
| WO | 03103611 | 12/2003 |
| WO | WO2004011021 | 2/2004 |
| WO | WO2004011632 | 2/2004 |
| WO | 2004 045592 | 6/2004 |
| WO | WO2006037233 | 4/2006 |
| WO | WO 2007106987 | 9/2007 |
| WO | WO2009057111 | 5/2009 |
| WO | WO 2009/137874 | 11/2009 |

OTHER PUBLICATIONS

English translation of RU 2003339 C1. Russian Federation Committee for Patents and Trademarks. Published Nov. 30, 1993.

Torner et al. "Prolactin Prevents Chronic Stress-Induced Decrease of Adult Hippocampal Neurogenesis and Promotes Neuronal Fate." *The Journal of Neuroscience*. 29(6): 1826-1833. Feb. 11, 2009.

Webber et al. "Gonadotropins and Alzheimer's Disease: the Link Between Estrogen Replacement Therapy and Neuroprotection." *Acta Neurobiol Exp*. 2004, 64: 113-118.

Lei et al., "Novel expression of human chorionic gonadotropin/luteinizing hormone receptor gene in brain," Endocrinology. May 1993, 132(5). pp. 2262-2270.

Minnerup et al., "The Efficacy of Erythropoietin and Its Analogues in Animal Stroke Models: A Meta-Analysis," American Heart Association, Inc. pp. 3113-3120. 2009.

Belayev et al., "A novel neurotrophic therapeutic strategy for experimental stroke," Brain Research 1280: 117-123, 2009.

Barron, A. et al. "Time- and Dose-Dependent Effects of Ovariectomy and Human Chorionic Gonadotropin Treatment on Beta Amyloid and Isoprostane Levels in the PS1M146V Mouse Model of Alzheimer's Disease." p. 1-436. ICAD Jul./Aug. 2008.

Belayev, L. et al. "Neuroprotective Effect of Human Chorionic Gonadotropin in Transient Focal Cerebral Ischemia in Rats," Poster. International Stroke Conference. San Antonio, TX, Feb. 23-26, 2010.

Belayev, L. et al. "A novel neurotrophic therapeutic strategy for experimental stroke." Brain Research 1280 pp. 117-123 (2009).

Choi, H.K. and Waxman, D. "Growth Hormone, but Not Prolactin, Maintains Low-Level Activation of STAT5a and STAT5b in Female Rat Liver." Endocrinology 140: 5126-5135, 1999.

Chojnacki, A. and Weiss, S., "Experssion and putative function of MASH1 and MASH2 in EGF-responsive forebrain neural stem cells." Society for Neuroscience, Presentation No. 600.14 Nov. 8, 2000. (abstract).

Cramer, S. et al. "The Beta-hCG + Erythropoietin in Acute Stroke (BETAS) Study. A 3-Center, Single Dose, Open-Label, Noncontrolled, Phase IIa Safety Trial," Stroke. pp. 1-4. Published online Mar. 4, 2010.

Curtis, M. et al. "Neurogenesis in the Diseased Adult Human Brain," Cell Cycle 2:5, 428-430; Sep./Oct. 2003.

Davidoff, A.W. et al., "Open labeled, uncontrolled pharmacokinetic study of a single intramuscular hCG dose in healthy male volunteers." International Journal of Clinical Pharmacology and Therapeutics, vol. 47: 1-9, Jul. 5, 2009.

Eriksson, P. et al., "Neurogenesis in the adult human hippocampus," Nature Medicine, vol. 4, No. 11: 1313-1317. Nov. 1998.

Faden, A. et al. "Treatment of experimental stroke: Comparison of naloxone and thyrotropin releasing hormone." Neurology 1982; 32: 1083-7.

Garber, Ken. "Stroke treatment—light at the end of the tunnel?" Nature Biotechnology vol. 25, No. 8, Aug. 2007.

Kolb, B. et al. "Growth factor-stimulated generation of new cortical tissue and functional recovery after stroke damage to the motor cortex of rats." Journal of Cerebral Blood Flow & Metabolism. pp. 1-15, 2006.

Le Cotonnec, J.Y. et al., "Clinical pharmacology of recombinant human luteinizing hormone: Part II. Bioavailability of recombinant human luteinizing hormone assessed with an immunoassay and an in vitro bioassay," Fertility and Sterility vol. 69, No. 2 Feb. 1998.

Mannaerts, B.M.J.L. et al., "A randomized three-way cross-over study in healthy pituitary-suppressed women to compare the bioavailability of human chorionic gonadotrophin (Pregnyl) after intramuscular and subcutaneous administration," Human Reproduction vol. 13 No. 6 pp. 1461-1464, 1998.

Markianos, M. et al. "Serum and Cerebrospinal Fluid Prolactin levels in Male and Female Patients with Clinically-Isolated Syndrome or Relapsing-Remitting Multiple Sclerosis." Journal of Neuroendrocrinology 2010; 22: 503-508.

Sato, A. et al., "Cystine Knot of the Gonadotropin a Subunit Is Critical for Intracellular Behavior but Not for in Vitro Biological Activity," The Journal of Biological Chemistry. vol. 272, No. 29, Issue of Jul. 18, pp. 18098-18103, 1997.

Wehmann, R. and Nisula, B. "Metabolic and Renal Clearance Rates of Purified Human Chorionic Gonadotropin." J. Clin. Invest. copyright The American Society for Clinical Investigation Inc. 0021-9738/81/07/0184/11 vol. 68, pp. 184-194. Jul. 1981.

Woody et al., "Prolactin exerts hematopoietic growth-promoting effects in vivo and partially counteracts myelosuppression by azidothymidine," Experimental Hematology 27: 811-816. 1999.

XP-002582723, NCT00362414 on Aug. 9, 2006: ClinicalTrials.gov Archive.

Ehrenreich et al., "Recombinant Human Erythropoietin in the Treatment of Acute Ischemic Stroke," Stroke. 2009; 40:00-00.

Aberg et al., "Peripheral Infusion of IGF-I Selectively Induces Neurogenesis in the Adult Rat Hippocampus," J. Neurosci. 20(8):2896-2904 (2000).

Abramsky et al., "Suppressive Effect of Pregnancy on Ms and EAE," Prog. Clin. Biol. Res. 146:399-406 (1984).

Al-Hader et al, "Neurons from fetal rat brain contains functional luteinizing hormone/chorionic gonadotropin receptors," Bio. Reprod. 56:1071-6 (1997).

Al-Hader et al., "Novel expression of functional luteinizing hormone/chorionic gonadotropin receptors in cultured glial cells from neonatal rat brains," Bio. Reprod. 56:501-507 (1997).

Allen et al., "Sexual dimorphism and asymmetries in the gray-white composition of the human cerebrum," NeuroImage 18:880-894 (2003).

Anderson et al., "Insulin-like growth factor-1 and neurogenesis in the adult mammalian brain," Brain Res. Dev. Brain Res. 134(1-2):115-22 (2002).

Arimura et al., "PACAP functions as a neurotrophic factor," Ann. N.Y. Acad. Sci. 739:228-243 (1994).

Arimura et al., "Perspectives on pituitary adenylate cyclase activating polypeptide PACAP in the neuroendocrine, endocrine and nervous systems," Jap. J. Physiol. 48:301-331 (1998).

Arimura et al., "Tissue Distribution of PACAP as Determined by RIA: Highly Abundant in the Rat Brain Testes," Endocrinol. 129:2787-2789 (1991).

Arimura, "Pituitary adenylate cyclase activating polypeptide PACAP: Discovery and current status of research," Regulatory Peptides 37:287-303 (1992).

Arlotta et al, "Introduction to Adult Neurogensis," Ann. N.Y. Acad. Sci. 991:229-236 (2003).

Armstrong et al., "Absence of fibroblast growth factor 2 promotes oligodendroglial repopulation of demyelinated white matter," J. Neurosci. 22(19):8574-8585 (2002).

Arnett et al., "TNFα promotes proliferation of oligodendrocyte progenitors and remyelination," Nature 4(11):1116-22 (2001).

Arsenijevic and Weiss, "Insulin-like Growth Factor-1 (IGF-I) Recruits a Distinct Population of Embryonic Neural Stem Cells," Mol. Biol. Cell 7(Supplement):1842 (1996).

Arsenijevic et al., "Insulin-like growth factor-I is necessary for neural stem cell proliferation and demonstrates distinct actions of epidermal growth factor and fibroblast growth factor-2," J. Neurosci. 21(18):7194-202 (2001).

Aston et al., "Transcriptional profiling reveals evidence for signaling and oligodendroglial abnormalities in the temporal cortex from patients with major depressive disorder," Mol. Psychiatry 10:309-322 (2005).

Bambakidis and Miller, "Transplantation of oligodendrocyte precursors and sonic hedgehog results in improved function and white matter sparing in the spinal cords of adult rats after contusion," J. Spine 4:16-26 (2004).

Banks et al., "Passage of pituitaty adenylate cyclase activating polypeptide 1-27 and pituitary adenylate cyclase polypeptide 1-38 across the blood-brain barrier," J. Pharmacol. Exp. Ther. 267:690-6 (1993).

Bartzokis et al., "Heterogeneous age-related breakdown of white matter structural integrity: implications for cortical 'disconnection,' in aging and Alzheimer's disease" Neurobiol. Aging 25:843-851 (2004).

Bayer, "Neuron production in the hippocampus and olfactory bulb of the adult rat brain: Addition or replacement?," Ann. N.Y. Acad. Sci. 457:163-73 (1985).

Bebo, Jr. and Dveksler, "Evidence that pregnancy specific glycoproteins regulate T-Cell function and inflammatory autoimmune disease during pregnancy," Curr. Drug Targets Inflamm. & Allergy 4:231-273 (2005).

Bebo, Jr. et al., "Low-dose estrogen therapy ameliorates experimental autoimmune encephalomyelitis in two different inbred mouse strains," J. Immunol. 166:2080-2089 (2001).

Bernichtein et al., "S179D-human PRL, a pseudophosphorylated human PRL analog, is an agonist and not an antagonist," Endocrinology 142(9):3950-3963 (2001).

Bithell, "Neural Stem Cells and Replacement Therapy: Making the right cells," Clin. Sci., 108:13-22 (2003).

Brannvall et al., "Estrogen-receptor-dependent regulation of neural stem cell proliferation and differentiation," Mol. Cell. Neurosci. 21(3):512-20 (2002).

Brown, "Enriched environment and physical activity stimulate hippocampal but not olfactory bulb neurogenesis," Eur. J. Neurosci. 17(10):2042-2046 (2003).

Brück and Stadelmann, "The spectrum of multiple sclerosis: new lessons from pathology," Curr. Opin. Neurol. 18:221-224 (2005).

Buckner, "Memory and executive function in aging and AD: multiple factors that cause decline and reserve factors that compensate," Neuron 44:195-208 (2004).

Camarillo et al., "Prolactin receptor expression in the epithelia and stroma of the rat mammary gland," J. Endocrinol. 171:85-95 (2001).

Cao et al., "Functional recovery in traumatic spinal cord injury after transplantation of multineurotrophin-expressing glial-restricted precursor cells," J. Neurosci. 25(30):6947-6957 (2005).

Carey et al., "Pituitary Adenylate Cyclase Activating Polypeptide Antimitogenic Signaling in Cerebral Cortical Progenitors is Regulated by p57Kip2-dependent CDK2 activity," J. Neurosci. 22(5):1583-91 (2002).

Cerami et al., "Effects of Epoetin Alfa on the Central Nervous System," Seminars in Oncology 28(2):66-70 (2001).

Cerghet et al., "Proliferation and death of oligodendrocytes and myelin proteins are differentially regulated in male and female rodents," J. Neurosci. 26(5):1439-1447 (2006).

Chikanza, "Prolactin and neuroimmunomodulation: in vitro and in vivo observations," Ann. N.Y. Acad. Sci. 876:119-130 (1999).

Chojnacki and Weiss, "Isolation of a novel platelet-derived growth factor-responsive precursor from the embryonic ventral forebrain," J. Neurosci. 24:10888-10899 (2004).

Christophe, "Type I Receptors for PACAP (a neuropeptide even more important than VIP?)," Biochim. Biophys. Acta 1154:183-99 (1993).

Confavreux et al., "Rate of pregnancy-related relapse in multiple sclerosis," N. Engl. J. Med. 339(5):285-91 (1998).

Craig et al., "In vivo growth factor expansion of endogenous subependymal neural precursor cell populations in adult mouse brain," J. Neurosci. 16:2649-58 (1996).

Cunningham et al., "High-resolution epitope mapping of hGH-receptor interactions by alanine-scanning mutagenesis," Science 244(4908):1081-5 (1989a).

Cunningham et al., "Receptor and antibody epitopes in human growth hormone identified by homolog-scanning mutagenesis," Science 243(4896):1330-1336 (1989b).

Curtis, "Neurogenisis in the diseased adult human brain," Cell Cycle, 2(5):428-430 (2003).

Dawson et al., "NG2-expressing glial progenitor cells an abundant and widespread population of cycling cells in the adult rat CNS," Mol. Cell. Neurosci. 24:476-488 (2003).

DeVito et al., "Prolactin induced expression of interleukin-1 alpha, tumor necrosis factoralpha, and transforming growth factor-alpha in cultured astrocytes," J. Cell Biochem. 57:290-298 (1995).

Dicicco-Bloom et al., "The PACAP Ligand/Receptor System Regulates Cerebral Cortical Neurogenesis," Ann. N.Y. Acad. Sci. 11:274-289 (1998).

Dong and Greenough, "Plasticity of nonneuronal brain tissue: roles in developmental disorders," Ment. Retard. Dev. Disabil. Res. Rev. 10:85-90 (2004).

Draca and Levic, "The possible role of prolactin in the immunopathogenesis of multiple sclerosis," Med. Hypotheses 47:89-92 (1996).

Dubey et al., "Differential penetration of three anterior pituitary peptide hormones into the cerebrospinal fluid of rhesus monkeys," Life Sci. 32(16):1817-1863 (1983).

Dulac and Torello, "Molecular detection of pheromone signals in mammals: from genes to behaviour," Nat. Rev. Neurosci., 4(7):551-562 (2003).

Faulkner and Keirstead, "Human embryonic stem cell-derived oligodendrocyte progenitors for the treatment of spinal cord injury," Transpl. Immunol. 15:131-142 (2005).

Fernandez-Pol, "Epidermal growth factor receptor of A431 cells. Characterization of a monoclonal anti-receptor antibody noncompetitive agonist of epidermal growth factor action," J. Biol. Chem. 260(8):5003-5011 (1985).

Ferro and Madureira, "Age-related white matter changes and cognitive impairment," Neurol. Sci. 203-204:221-225 (2002).

Fields, "Myelination: an overlooked mechanism of synaptic plasticity?," Neuroscientist 11(6):528-531 (2005).

Fleming and Walsh, "Neuropsychology of maternal behavior in the rat: c-fos expression during mother-litter interactions," Psychoneuroendocrinology 19(5-7):429-443 (1994).

Fowler et al, "The effects of social environment on adult neurogenesis in the female prairie vole," J. Neurobiol. 51(2):115-128 (2002).

Freed et al., "Survival of Implanted Fetal Dopamine Cells and Neurologic Improvement 12 to 46 Months After Transplantation for Parkinson's Disease," N. Engl. J. Med. 327:1549-1555 (1992).

Freeman et al., "Prolactin: structure, function and regulation of secretion," Physiol. Rev. 80: 1523-1631 (2000).

Frisen et al., "Central nervous system stem cells in the embryo and adult," Cell. Mol. Life Sci. 54(9):935-945 (1998).

Gage et al., "Isolation, characterization, and use of stem cells from the CNS," Annu. Rev. Neurosci. 18:159-92 (1995).

Gage, "Mammalian neural stem cells," Science 287(5457):1433-1438 (2000).

Gage et al., "Survival and differentiation of adult neuronal progenitor cells transplanted to the adult brain," Proc. Natl. Acad. Sci. USA 92(25):11879-83 (1995).

Gatewood et al., "Motherhood mitigates aging-related decrements in learning and memory and positively affects brain aging in the rat," Brain Res. Bull. 66:91-98 (2005).

Gensert and Goldman, "In vivo characterization of endogenous proliferating cells in adult rat subcortical white matter," Glia 17:39-51 (1996).

Gensert and Goldman, "Endogenous progenitors remyelinate demyelinated axons in the adult CNS," Neuron 19:197-203 (1997).

Goeddel et al., "Direct expression in *Escherichia coli* of a DNA sequence coding for human growth hormone," Nature 281(5732):544-548 (1979).

Goffin et al., "Sequence-Function Relationships within the Expanding Family of Prolactin, Growth Hormone, Placental Lactogen, and Related Proteins in Mammals," Endocrine Reviews 17:385-410 (2007).

Gray et al., "Periplasmic production of correctly processed human growth hormone in *Escherichia coli*: natural and bacterial signal sequences are interchangeable," Gene 39(2-3):247-254 (1985).

Gur et al., "Sex differences in brain gray and white matter in healthy young adults: correlations with cognitive performance," J. Neurosci. 19(10):4065-4072 (1999).

Hack et al., "Neuronal fate determinants of adult olfactory bulb neurogenesis," Nat. Neurosci. 8(7):865-872 (2005).

Haier et al., "The neuroanatomy of general intelligence: sex matters," Neuroimage 25:320-327 (2005).

Hansel et al., "Regulation of Olfactory Neurogenesis by Amidated Neuropeptides," J. Neurosci. Res. 66:1-7 (2001).

Hashimoto et al., "Altered Psychomotor Behaviors in Mice Lacking Pituitary Adenylate Cyclase-Activating Polypeptide (PACAP)," Proc. Natl. Acad. Sci. USA 98:(23)13355-13360 (2001).

Hashimoto et al., "Molecular Cloning and Tissue Distribution of a Receptor for Pituitary Adenylate Cyclase Activating Polypeptide," Neuron 11:333-342 (1993).

Hirose et al., "Gene expression of PACAP and its receptors in the ES cell-derived neuronal stem cells," Japanese J. Pharmacol. 88:143 (Supplement 1) (2002).

Huhtaniemi et al., "Transgenic and knockout mouse models for the study of luteinizing hormone and luteinizing hormone receptor function," Mol. Cell. Endocrinol. 187(1-2):49-56 (2002).

Inzitari, "Leukoaraiosis: an independent risk factor for stroke?," Stroke 34:2067-2071 (2003).

Ito et al., "Estrogen treatment down-regulates TNF a production and reduces the severity of experimental autoimmune encephalomyelitis in cytokine knockout mice," J. Immunol. 167:542-552 (2001).

Jin et al., "Alzheimer's disease drugs promote neurogenesis," Brain Res. 1085(1):183-8 (2006).

Johnson, et al., "Erythropoietin mimetic peptides and the future," Nephrol. Dial. Transplant. 15(9):1274-1277 (2000).

Johnson et al., "Evaluating the Role of the Hormone Prolactin in Neuroinflammation and repair associated with experimental autoimmune encephalomyelitis," EndMS Research Conference, Banff, Alberta Canada, Dec. 10-13, 2007.

Jokinen et al., "Medial temporal lobe atrophy and memory deficits in elderly stroke patients," Eur. J. Neurol. 11:825-832 (2004).

Kandel et al. (eds.), "Principles of Neural Science," 3d Ed., p. 981, Elsevier Science Publishing Co., New York (1991).

Kaplan, "Neurogenesis in the 3-month Old Rat Visual Cortex," J. Comp. Neurol. 195:323-338 (1981).

Karbanova et al., "Neural stem cells transplanted into intact brains as neurospheres form solid grafts composed of neurons, astrocytes and oligodendrocyte precursors," Biomed. Papers 148(2):217-220 (2004).

Karimi-Abdolrezaee et al., "Delayed transplantation of adult neural precursor cells promotes remyelination and functional neurological recovery after spinal cord injury," J. Neurosci. 26(13):3377-3389 (2006).

Kaushansky, "Hematopoietic growth factor mimetics," Ann. N.Y. Acad. Sci. 938:131-138(2001).

Kempermann and Gage, "Experience-dependent regulation of adult hippocampal neurogenesis: effects of long-term stimulation and stimulus withdrawal," Hippocampus 9(3):321-332 (1999).

Keirstead et al., "Human embryonic stem cell-derived oligodendrocyte progenitor cell transplants remyelinate and restore locomotion after spinal cord injury," J. Neurosci. 25(19):4694-4075 (2005).

Kieseier et al., "Multiple sclerosis-novel insights and new therapeutic strategies," Curr. Opin. Neurol. 18:211-220 (2005).

Kim and Juraska, "Sex differences in the development of axon number in the splenium of the rat corpus callosum from postnatal day 15 through 60," Brain Res. Dev. Brain Res. 102:77 (1997).

Kim et al., "Estriol ameliorates autoimmune demyelinating disease: implications for multiple sclerosis," Neurology 52:1230-1238 (1999).

Kimura et al., "A Novel Peptide Which Stimulates Adenylate Cyclase: Molecular Cloning and Characterization of the Ovine and Human cDNAs," Biochem. Biophys. Res. Comm. 166:81-89 (1990).

Kinsley et al., "Motherhood improves learning and memory," Nature 402:137-138 (1999).

Kiyokawa et al., "Modulatory role of testosterone in alarm pheromone release by male rats," Horm. Behav. 45(2):122-127 (2004).

Kolb et al, "Growth factor-stimulated generation of new cortical tissue and functional recovery after stroke damage to the motor cortex of rats," J. Cerebral Blood Flow & Metabolism 27(5):983-7 (2007).

Kolb et al., "Nerve growth factor treatment prevents dendritic atrophy and promotes recovery of function after cortical injury," Neuroscience 76(4):1139-1151 (1996).

Konishi et al., "Tropic effect of erythropoietin and other hematopoietic factors on central cholinergic neurons in vitro and in vivo," Brain Res. 609:29-35 (1993).

Kovacs et al., "Olfactory Bulb in Multiple System Atrophy," Movement Disorder 18(8):938-942 (2003).

Lambert et al., "Pup exposure differentially enhances foraging ability in primiparous and nulliparous rats," Physiol. Behav. 84:799-806 (2005).

Learish et al., "Intraventricular transplantation of oligodendrocyte progenitors into a fetal myelin mutant results in widespread formation of myelin," Ann. Neurol. 46:716-722 (1999).

Lee et al., "Pituitary Adenylyl Cyclase-Activating Polypeptide Stimulates DNA Synthesis but Delays Maturation of Oligodendrocyte Progenitors," J. Neurosci. 21(11):3849-3859 (2001).

Lee et al., "Effects of glial transplantation on functional recovery following acute spinal cord injury," J. Neurotrauma 22(5):575-589 (2005).

Lei et al., "Neural actions of luteinizing hormone and human chorionic gonadotropin," Seminars in Reprod. Med. 19(1):103-109 (2001).

Lelievre et al., "Cross-talk between PACAP and sonic hedgehog (SHH) pathways in neural stem cells, cerebellar granular progenitor cells and oligodendrocyte progenitors to control cell fate and proliferation," Regulatory Peptides 115(1):50 (2003).

Lelievre et al., "Fibroblast growth factor-2 converts PACAP growth action on embryonic hindbrain precursors from stimulation to inhibition," J. Neurosci. Res. 67(5):566-573 (2002).

Lelievre et al., "Interactive of PACAP with sonic Hedgehog on neural stem cell and oligodendrocyte progenitor proliferation," J. Neurochem. 85:66 (Supplement 1) (2003).

Levine et al., "The oligodendrocyte precursor cell in health and disease," Trends Neurosci. 24(1):39-47 (2001).

Levison et al., "Cycling cells in the adult rat neocortex preferentially generate oligodendroglia," J. Neurosci. Res. 57:435-466 (1999).

Lim et al., "Noggin antagonizes BMP signaling to create a niche for adult neurogenesis," Neuron 28:713-726 (2000).

Lindholm et al., "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci. 865:189-196 (1998).

Livnah et al., "Functional mimicry of a protein hormone by a peptide agonist: the EPO receptor complex at 2.8 Å," Science 273(5274):464-471 (1996).

Lledo et al., "Adult neurogenesis and functional plasticity in neuronal circuits," Nat. Rev. Neurosci. 7:179-193 (2006).

Lobie et al., "Growth hormone, insulin-like growth factor I and the CNS: localization, function and mechanism of action," Growth Horm. IGF Res. (Supplement B):S51-S56 (2000).

Love et al., "Maternal experience produces long-lasting behavioral modification in the rat," Behav. Neurosci. 119(4):1084-1096 (2005).

Lowman et al., "Mutational analysis and protein engineering of receptor-binding determinants in human placental lactogen," J. Biol. Chem. 266:10982-10988 (1991).

Lu et al., "Pituitary Adenylate Cyclase-Activating Polypeptide is an Autocrine Inhibitor of Mitosis in cultured Cortical Precursor Cells," Proc. Natl. Acad. Sci. USA 94:3357-3362 (1997).

Lubetzki et al., "Promoting repair in multiple sclerosis: problems and prospects," Curr. Opin. Neurol. 18:237-244 (2005).

Luskin, "Restricted proliferation and migration of postnatally generated neurons derived from the forebrain subventricular zone," Neuron 11(1):173-189 (1993).

Lyoo et al., "White matter hyperintensities on magnetic resonance imaging of the brain in children with psychiatric disorders," Compr. Psychiatry 43(5):361-368 (2002).

Ma et al., "Role of the adrenal gland and adrenal-mediated chemosignals in suppression of estrus in the house mouse: The leeboot effect revisited," Biol. Reprod. 59(6):1317-1320 (1998).

Mack et al., "Sex differences in the distribution of axon types within the genu of the rat corpus callosum," Brain Res. 697:152-156 (1995).

Menezes et al., "The division of neuronal progenitor cells during migration in the neonatal mammalian forebrain," Mol. Cell. Neurosci., 6(6):496-508 (1995).

Menn et al., "Origin of oligodendrocytes in the subventricular zone of the adult brain," J. Neurosci. 26(30):7907-7918 (2006).

Misra et al, "Drug Delivery to the central nervous system: a review," J. Pharm. Pharmaceut. Sci. 6(2):252-73 (2003).

Miyata et al., "Isolation of a Novel 38 Residue-Hypothalamic Polypeptide which Stimulates Adenylate Cyclase in Pituitary Cells," Biochem. Biophys. Res. Comm. 164:567-574 (1989).

Mode et al., "The human growth hormone (hGH) antagonist G120RhGH does not antagonize GH in the rat, but has paradoxical agonist activity, probably via the prolactin receptor," Endocrinology 137(2):447-454 (1996).

Moderscheim et al., "Prolactin is Involved in Glial Responses Following a Focal Injury to the Juvenile Rat Brain," Neuroscience 145: 963-973 (2007).

Moore et al., "Cerebral white matter lesions in bipolar affective disorder: relationship to outcome," Br. J. Psychiatry 178:172-176 (2001).

Mori, "Impact of subcortical ischemic lesions on behavior and cognition," Ann. N.Y. Acad. Sci. 977:141-148 (2002).

Moro et al., "Maxadilan, the vasodilator from sand flies, is a specific pituitary adenylate cyclase activating peptide type I receptor agonist," J. Biol. Chem. 272(2): 966-70 (1997).

Morrison et al., "Regulatory mechanisms in stem cell biology," Cell 88:287-298 (1997).

Morshead and Van Der Kooy, "Postmitotic death is the fate of constitutively proliferating cells in the subependymal layer of the adult mouse brain," J. Neurosci. 12(1):249-256 (1992).

Mulloy et al., "Absorption or orally administered bovine prolactin by neonatal rats," Biol. Neonate 36(3-4):148-53 (1979).

Nait-Oumesmar et al., "Progenitor cells of the adult mouse subventricular zone proliferate, migrate and differentiate into oligodendrocytes after demyelination," Eur. J. Neurosci. 11:4357-4366 (1999).

Neumann, "Alterations in behavioral and neuroendocrine stress coping strategies in pregnant, parturient and lactating rats," Prog. Brain Res. 133:143-152 (2001).

Nicot et al., "Regulation of Neuroblast Mitosis is Determined by PACAP Receptor Isoform Expression," Proc. Natl. Acad. Sci. USA 98:(8)4758-4763 (2001).

Nilsson et al., "Enriched environment increased neurogenesis in the adult rat dentate gyrus and improves spatial memory," J. Neurobiol. 39(4):569-578 (1999).

Nuñez et al., "Myelination in the splenium of the corpus callosum in adult male and female rats," Dev. Brain Res. 120:87-90 (2000).

Nyberg, "Aging effects on growth hormone receptor binding in the brain," Exp. Gerontol. 32:521-528 (1997).

Nyberg, "Growth hormone in the brain: characteristics of specific brain targets for the hormone and their functional significance," Front. Neuroendocrinol. 21:330-348 (2000).

Ohta et al., "Pituitary adenylate cyclase-activating polypeptide (PACAP) regulates forebrain neural stem cell fate in vitro and in vivo," Society for Neuroscience Abstract Viewer and Itinerary Planner 2002:329.13 (2002).

Ormandy et al., "Null mutation of the prolactin receptor gene produces multiple reproductive defects in the mouse," Genes Dev. 11:167-178 (1997).

Ostenfeld et al., "Recent Advances in Stem Cell Neurobiology," Adv. Tech. Stand. Neurosurg. 28:3-89 (2003).

Otto et al., "Altered Emotional Behavior in PACAP-type-I-receptor-deficient Mice," Brain Res. Mol. Brain Res. 91(1-2):78-84 (2001).

Park, "Transplantation of neural stem cells: cellular & gene therapy for hypoxic-ischemic brain injury," Yonsei Med. J. 41(6):825-835 (2000).

Parker et al, "Expression profile of an operationally-defined neural stem cell clone," Exper. Neuro. 194:320-332 (2005).

Patil, "The effect of Human Chorionic Gonadotropin (HCG) on Restoration of Physiological Continuity of the Spinal Cord. A Preliminary Report," Int. Surg. 75:54-57 (1990).

Patil, "The Study of the Effect of Human Chorionic Gonadotrophic (HCG) Hormone on the Survival of Adrenal Medulla Transport in Brain. Preliminary Study," Acta Neurochirurgica 87:76-8 (1987).

Patil and Nagaraj, "The Effect of Human Chorionic Gonadotropin (HCG) on Functional Recovery of Spinal Cord Sectioned Rats*," Acta Neurochirurgica 69:205-18 (1983).

Patil and Nagaraj, Letter to the Editor, Neurosurgery 12(5):593-4 (1983).

Peretto et al., "The subependymal layer in rodents: a site of structural plasticity and cell migration in the adult mammalian brain," Brain Res. Bull. 49(4):221-243 (1999).

Perlow et al., "Brain Grafts Reduce Motor Abnormalities Produced by Destruction of Nigrostriatal Dopamine System," Science 204:643-647 (1979).

Pesce et al., "Pituitary adenylate cyclass-activating polypeptide (PACAP) stimulates adenylate cyclase and promotes proliferation of mouse primordial germ cells," Development 122(1):215-221 (1996).
Peters and Sethares, "Oligodendrocytes, their progenitors and other neuroglial cells in the aging primate cerebral cortex," Cereb. Cortex 14:995-1007 (2004).
Peters et al., "Effects of aging on the neuroglial cells and pericytes within area 17 of the rhesus monkey cerebral cortex," Anat. Rec. 229:384-398 (1991).
Peters, "The effects of normal aging on myelin and nerve fibers: a review," J. Neurocytol. 31:581-593 (2002).
Phelps et al., "Stimulatory effect of human, but not bovine, growth hormone expression on numbers of tuberoinfundibular dopaminergic neurons in transgenic mice," Endocrinology 138(7):2849-2855 (1997).
Phelps et al., "Pituitary hormones as neurotrophic signals: Update on hypothalamic differentiation in genetic models of altered feedback," Proc. Soc. Exper. Bio. Med. 222(1):39-58 (1999).
Picard-Riera et al., "Experimental autoimmune encephalomyelitis mobilizes neural progenitors from the subventricular zone to undergo oligodendrogenesis in adult mice," Proc. Natl. Acad. Sci. USA 99(20):13211-13216 (2002).
Pluchino et al, "Injection of adult neurospheres induces recovery in a chronic model of multiple sclerosis," Nature 422(6933):688-94 (2003).
Polito and Reynolds, "NG2 expressing cells as oligodendrocyte progenitors in the normal and demyelinated adult central nervous system," Anat. 207:707-716 (2005).
Potten and Loeffler, "Stem Cells: Attributes, Cycles, Spirals, Pitfalls and Uncertainties. Lessons for and from the Crypt," Development 110:1001-1020 (1990).
Rakic, "Limits of Neurogenesis in Primates," Science 227:1054-1056 (1985).
Rawlings, "At the Cutting Edge PACAP, PACAP Receptors, and Intracellular Signalling," Mol. Cell. Endocrinol. 191:C5-C9 (1994).
Rao, "Multipotent and restricted precursors in the central nervous system," Anat. Rec. 257(4):137-148 (1999).
Reynolds and Weiss, "Generation of Neurons and Astrocytes from Isolated Cells of the Adult Mammalian Central Nervous System," Science 255:1701-1710 (1992).
Reynolds and Weiss, "Clonal and population analyses demonstrate that an EGF-responsive mammalian embryonic CNS precursor is a stem cell," Develop. Bio. 175:1-13 (1996).
Reynolds et al., "Ethanol modulation of GABA receptor-activated Cl-currents in neurons of the chick, rat and mouse central nervous system," Eur. J. Pharmacol. 224(2-3):173-181 (1992).
Rietze et al., "Mitotically Active Cells that Generate Neurons and Astrocytes are Present in Multiple Regions of the Adult Mouse Hippocampus," J. Comp. Neurol. 424(3):397-408 (2000).
Rochefort et al., "Enriched odor exposure increases the number of newborn neurons in the adult olfactory bulb and improves odor memory," J. Neurosci. 22(7):2679-2689 (2002).
Rodriguez-Pena, "Oligodendrocyte development and thyroid hormone," J. Neurobiol. 40(4):497-512 (1999).
Rostene et al., "VIP and PAGAP via G-Protein coupled receptors are potent inducers of mouse embryonic stem cell neuronal differentiation," Regulatory Peptides 115(1):55 (2003).
Schanzer et al, "Direct Stimulation of Adult Neural Stem Cells in vitro and Neurogenesis in vivo by vascular Endothelial Growth Factor," Brain Path 14(3):237-48 (2004).
Scharfman et al, "Increased neurogenesis and the ectopic granuae cells after intrahippocampal BDNF infusion in rats," Exp. Neuro. 192(2):348-56 (2005).
Scheepens et al., "Growth Hormone as a Neuronal Rescue Factor During Recovery from CNS Injury," Neurosci. 104(3):677-687 (2001).
Schlessinger et al., "Crystal structure of a ternary FGF-FGFR-heparin complex reveals a dual role for heparin in FGFR binding and dimerization," Mol. Cell 6:743-50 (2000).
Schradin and Anzenberger, "Prolactin, the Hormone of Paternity," News Physiol. Sci. 14:223-231 (1999).
Scolding and Franklin, "Remyelination in demyelinating disease," Baillieres Clin. Neurol. 6:525-548 (1997).
Shimazaki et al., "The ciliary neurotrophic factodleukemia inhibitory factor/gp130 receptor complex operates in the maintenance of mammalian forebrain neural stem cells," J. Neurosci. 21(19):7642-7653 (2001).
Shingo et al., "Erythropoietin regulates the in vitro and in vivo production of neuronal progenitors by mammalian forebrain neural stem cells," J. Neurosci. 21(24):9733-9743 (2001).
Shingo et al., "Pregnancy-stimulated neurogenesis in the adult female forebrain mediated by prolactin," Science 299:117-120 (2003).
Shingo et al., Supporting Online Material pp. 1-10, "Pregnancy-Stimulated Neurogenesis in the Adult Female Forebrain Mediated by Prolactin," Science 299:117-20 (2003).
Shioda et al., "Pleiotropic functions of PACAP in the CNS. Neuroprotection and neurodevelopment," Ann. N.Y. Acad. Sci. 1070:550-60 (2006).
Sicotte et al., "Treatment of multiple sclerosis with the pregnancy hormone estriol," Ann. Neurol. 52:421-428 (2002).
Silverstone et al., "Deep white matter hyperintensities in patients with bipolar depression, unipolar depression and age-matched control subjects," Bipolar Disord. 5:53-57 (2003).
Sirevaag and Greenough, "Differential rearing effects on rat visual cortex synapses. III. Neuronal and glial nuclei, boutons, dendrites and capillaries," Brain Res. 424:320-322 (1987).
Sorokan et al., "Erythropoietin mediates increased neurogenesis by embryonic CNS stem cells following a modest hypoxic insult," Soc. Neurosci. 23(1/2):320 (1997).
Spencer et al., "Unilateral Transplantation of Human Fetal Mesencephalic Tissue into the Caudate Nucleus of Patients with Parkinson's Disease," N. Engl. J. Med. 327:1541-1548 (1992).
Stangel and Hartung, "Remyelinating strategies for the treatment of multiple sclerosis," Prog. Neurobiol. 68:361-376 (2002).
Stevens et al., "Adenosine: a neuron-glial transmitter promoting myelination in the CNS in response to action potentials," Neuron 36:855-868 (2002).
Studer et al., "Enhanced proliferation, survival, and dopaminergic differentiation of CNS precursors in lowered oxygen," J. Neurosci. 20(19):7377-7383 (2000).
Sturrock, "Myelination of the mouse corpus callosum," Neuropathol. Appl. Neurobiol. 6:415-420 (1980).
Szeligo and Leblond, "Response of the three main types of glial cells of cortex and corpus callosum in rats handled during suckling or exposed to enriched, control and impoverished environments following weaning," J. Comp. Neurol. 172:247-264 (1977).
Tanaka, "Potential of Use of Neural Stem Cells as Stroke as a Clinical Treatment," Juniendo Med. J. 52(1):2-10 (2006).
Tanapat et al., "Estrogen stimulates a transient increase in the number of new neurons in the dentate grus of the adult female rat," J. Neurosci. 19(14):5792-5801 (1999).
Tang et al., "Long-term culture of purified postnatal oligodendrocyte precursor cells. Evidence for an intrinsic maturation program that plays out over months," J. Cell Biol. 148:971-984 (2000).
Tauber et al., "Myelination in rabbit optic nerves is accelerated by artificial eye opening," Neurosci. Lett. 16:235-238 (1980).
The American Heritage Dictionary of the English Language 4th Ed., Dictionary.com/neural (2000).
Totoiu and Keirstead, "Spinal cord injury is accompanied by chronic progressive demyelination," J. Comp. Neurol. 486:373-383 (2005).
Tropepe et al., "Transforming growth factor-alpha null and senescent mice show decreased neural progenitor cell proliferation in the forebrain subependyma," J. Neurosci. 17:7850-7859 (1997).
Van Dam et al, "Growth Hormone, insulin-like growth factor I and cognitive function in adults," Growth Horm. IGF Res. (Supplement B):S69-73 (2000).
Van Der Kooy and Weiss, "Why Stem Cells?," Science 287:1439-41 (2000).
Van Walderveen et al., "Magnetic resonance evaluation of disease activity during pregnancy in multiple sclerosis," Neurology 44:327-329 (1994).
Vaudry et al., "Neurotrophic activity of pituitary adenylate cyclase-activating polypeptide on rate cerebellar cortex during development," Proc. Natl. Acad. Sci. USA 96(16):9415-9420 (1999).

Vaudry et al., "Pituitary Adenylate Cyclase-Activating Polypeptide and Its Receptors from Structure to Functions," Pharmacol. Rev. 52:269-324 (2000).

Voskuhl, "Hormone-based therapies in MS," Int. MS J. 10:60-66 (2003).

Walker et al., "Mother to infant or infant to mother? Reciprocal regulation of responsiveness to stress in rodents and the implications for humans," J. Psychiatry Neurosci. 29(5):364-382 (2004).

Wardlaw et al., "Is diffusion imaging appearance an independent predictor of outcome after ischemic stroke?," Neurology 59:1381-1387 (2002).

Waschek, "Multiple actions of pituitary adenylyl cyclase activating peptide in nervous system development and regeneration," Develop. Neurosci. 24:14-23 (2002).

Waschek, "VIP and PACAP Receptor-mediated Actions on Cell Proliferation and Survival," Ann. N.Y. Acad. Sci. 805:290-300 (1996).

Weetman, "The immunology of pregnancy," Thyroid 9(7):643-646 (1999).

Weiss et al., "Is there a neural stem cell in the mammalian forebrain?," Trends Neuro. 19:387-393 (1996).

Whittemore et al., "Mitogen and substrate differentially affect the lineage restriction of adult rat subventricular zone neural precursor cell populations," Exp. Cell Res. 252:75-95 (1999).

Widner et al., "Bilateral fetal Mesencephalic Grafting into Two Patients with Parkinsonism Induced by I-methyl-4-phenyl- 1,2,3,6-tetrahydropyridine (MPTP)," N. Engl. J. Med. 327:1556-1563 (1992).

Wrighton et al., "Small peptides as potent mimetics of the protein hormone erythropoietin," Science 273(5274):458-464 (1996).

Wu et al., "Expression of QKI proteins and MAP1B identifies actively myelinating oligodendrocytes in adult rat brain," Mol. Cell. Neurosci. 17:292-302 (2001).

Yuhara et al., "PACAP has a Neurotrophic Effect on Cultured Basal Forebrain Cholinergic Neurons from Adult Rats," Brain Res. Dev. Brain Res. 131(1):41-5 (2001).

Zhang et al., "Normal prenatal but arrested postnatal sexual development of luteinizing hormone receptor knockout (LuRKO) mice," Mol. Endocrinol. 15(1):172-183 (2007).

Zhang et al., "Scent, social status, and reproductive condition in rat-like hamsters (cricetulus triton)," Physiol Behav. 74(4-5):415-420 (2001).

Abstract of DE19905961 A1, "Use of estrogens to treat cardiac insufficiency and left ventricular dysfunction following myocardial infarction," Aug. 17, 2000.

Berlanga, J.J. et al., "Prolactin receptor is associated with c-src kinase in rat liver," Mol. Endocrinol. 1995, vol. 9, No. 11, p. 1461-7.

Database EPODOC European Patent Office, The Hague, NL; Jul. 18, 1998, XP002626863, Database accession No. JP1180833 abstract & JP 1 180833 A (Nippon Kayaku KK) Jul. 18, 1989.

Di, C.A. et al. "Characterization of prolactin receptor in human brain and choroid plexus," Brain Res., 1992, vol. 570, No. 1-2, p. 341-6.

Lei, Z.M. et al. "Novel expression of human chorionic gonadotropin/luteinizing hormone receptor gene in brain," Endocrinology, 1993, vol. 132, No. 5, p. 2262-70.

Mountjoy, K. et al. "Prolactin receptors in the rat kidney," J. Endrocrinol, 1980, vol. 87, No. 1, p. 47-54.

Ouhtit, A. et al. "Visualization of gene expression of short and long forms of prolactin receptor in the rat," Endocrinology, 1993, vol. 133, No. 1, p. 135-44.

Partial European Search Report in related European Application No. 11000912.3-1521. Apr. 12, 2011.

Sakaguchi, K. et al. "Differential regulation of prolactin receptor mRNA expression in rat liver and kidney by testosterone and oestradiol," J. Endocrinol, 1994, vol. 143, No. 2, p. 383-92.

Tsai-Morris, C. H. et al. "Structural organization of the rat luteinizing hormone (LH) receptor gene," J Biol Chem, 1991 vol. 266, No. 17, p. 11355-9.

\* cited by examiner

CONTINUOUS DOSING REGIMENS FOR NEURAL STEM CELL PROLIFERATING AGENTS AND NEURAL STEM CELL DIFFERENTIATING AGENTS

CROSS-REFERENCE TO RELATED APPLICATIONS

This application claims priority to and the benefit of U.S. Provisional Application Ser. No. 60/783,500, filed on Mar. 17, 2006; U.S. Provisional Application Ser. No. 60/789,132, filed on Apr. 5, 2006; and U.S. Provisional Application Ser. No. 60/862,669, filed on Oct. 24, 2006, which are incorporated herein by reference in their entireties.

BACKGROUND

The development of techniques for the isolation and in vitro culture of multipotent neural stem cells (for example, see U.S. Pat. Nos. 5,750,376; 5,980,885; 5,851,832) significantly improved the outlook for the treatment of neurodegenerative diseases and conditions. It was discovered that fetal brains can be used to isolate and culture multipotent neural stem cells in vitro. Moreover, in contrast to the long held belief that adult brain cells are not capable of replicating or regenerating brain cells, it was found that neural stem cells may also be isolated from brains of adult mammals. These stem cells, either from fetal or adult brains, are capable of self-replicating. The progeny cells can again proliferate or differentiate into any cell in the neural cell lineage, including neurons, astrocytes and oligodendrocytes. Therefore, these findings not only provide a source of neural cells which can be used in transplantations, but also demonstrate the presence of multipotent neural stem cells in adult brain and the possibility of producing neurons or glial cells from these stem cells in situ.

Certain molecules have been found to increase the number of neural stem cells in vitro or in vivo (see, e.g., U.S. Patent Application Publication Nos. 20050245436, 20040136967, 20040092448, 20030095956, 20030054998, 20030054551, 20030049838, 20030049837). The mechanisms for such increase may include stimulating proliferation, inhibiting differentiation, and/or preventing death of the neural stem cells. These molecules can thus be employed to produce neural stem cells, hence neurons and glial cells, in subjects in need of these cells.

SUMMARY

Provided herein are effective dosing regimens for neural stem cell proliferating agents and neural stem cell differentiating agents, kits, and uses thereof. In particular, neural stem cell proliferating agents are delivered to mammalian subjects at a low dose in a continuous fashion, as opposed to the administration of a high-dose in a short period of time. Such compositions of matter an methods can be utilized acutely (e.g., within days after neural injury or onset of neurologic symptoms) or can be used chronically (e.g., for persisting neural injury or ongoing neurologic symptoms).

Accordingly, provided herein are methods and kits for optimizing the efficacy of an effective amount of a neural stem cell proliferating agent in increasing the number of neural stem cells in a mammal, comprising administering the neural stem cell proliferating agent to the mammal continuously for a period of time, optionally by use of a kit, wherein the total dosage of the neural stem cell proliferating agent administered in said period of time equals the effective amount, and wherein said period of time is at least three days.

Also provided herein are methods and kits for optimizing the efficacy of an effective amount of a neural stem cell proliferating agent in treating or ameliorating a neurodegenerative disease or condition in a mammal, comprising administering the neural stem cell proliferating agent to the mammal continuously for a period of time, optionally by use of a kit, wherein the total dosage of the neural stem cell proliferating agent administered in said period of time equals the effective amount, and wherein said period of time is at least three days.

Further provided herein are methods and kits for treating or ameliorating a neurodegenerative disease or condition in a mammal is provided. The methods comprise administering an effective amount of a neural stem cell proliferating agent to the mammal continuously for a period of time, optionally by use of a kit, wherein said period of time is at least three days.

Additionally provided herein is a further method for treating or ameliorating a neurodegenerative disease or condition in a mammal. This method comprises administering to the mammal a neural stem cell proliferating agent and a neural stem cell differentiating agent, wherein the neural stem cell proliferating agent is administered continuously at least three times systemically over a first treatment period and wherein the neural stem cell differentiating agent is administered over a second treatment period, optionally by use of a kit. The neural stem cell proliferating agent and the neural stem cell differentiating agent can be administered continuously or intermittently. For example, a neural stem cell proliferating agent can be administered continuously on days 1, 2, and 3 of a first treatment period, then a neural stem cell differentiating agent can be administered continuously on days 1, 2, and 3 of a second treatment period.

In the methods and kits, the period of time may be, for example, at least three days. Optionally, the methods may comprise administering to the mammal the neural stem cell proliferating agent continuously in a second treating period, optionally by use of a kit, wherein the second treating period starts after the end of the period of time by an interval of at least one day, and wherein the second treating period is at least three days. The second treating period, like the first treating period, may be, for example, at least three days. This treating schedule can be repeated several times or many times with second, third, forth, fifth, etc. treating periods. This treating schedule, whether administered once, twice, several, or many times, can take the form of one or more kits, wherein an effective amount of neural stem cell proliferating agent and optionally a neural stem cell differentiating agent is provided for administration for a specified treating period or plurality of treating periods.

The details of methods and kits are set forth in the accompanying drawings and the description below. Other features, objects, and advantages of the methods and kits will be apparent from the description and drawings, and from the claims.

15×=**p<0.01; 20×=p<0.05; n=3 for all conditions; one way analysis of variance (ANOVA) with Tukey posthoc test.

Figure 2:
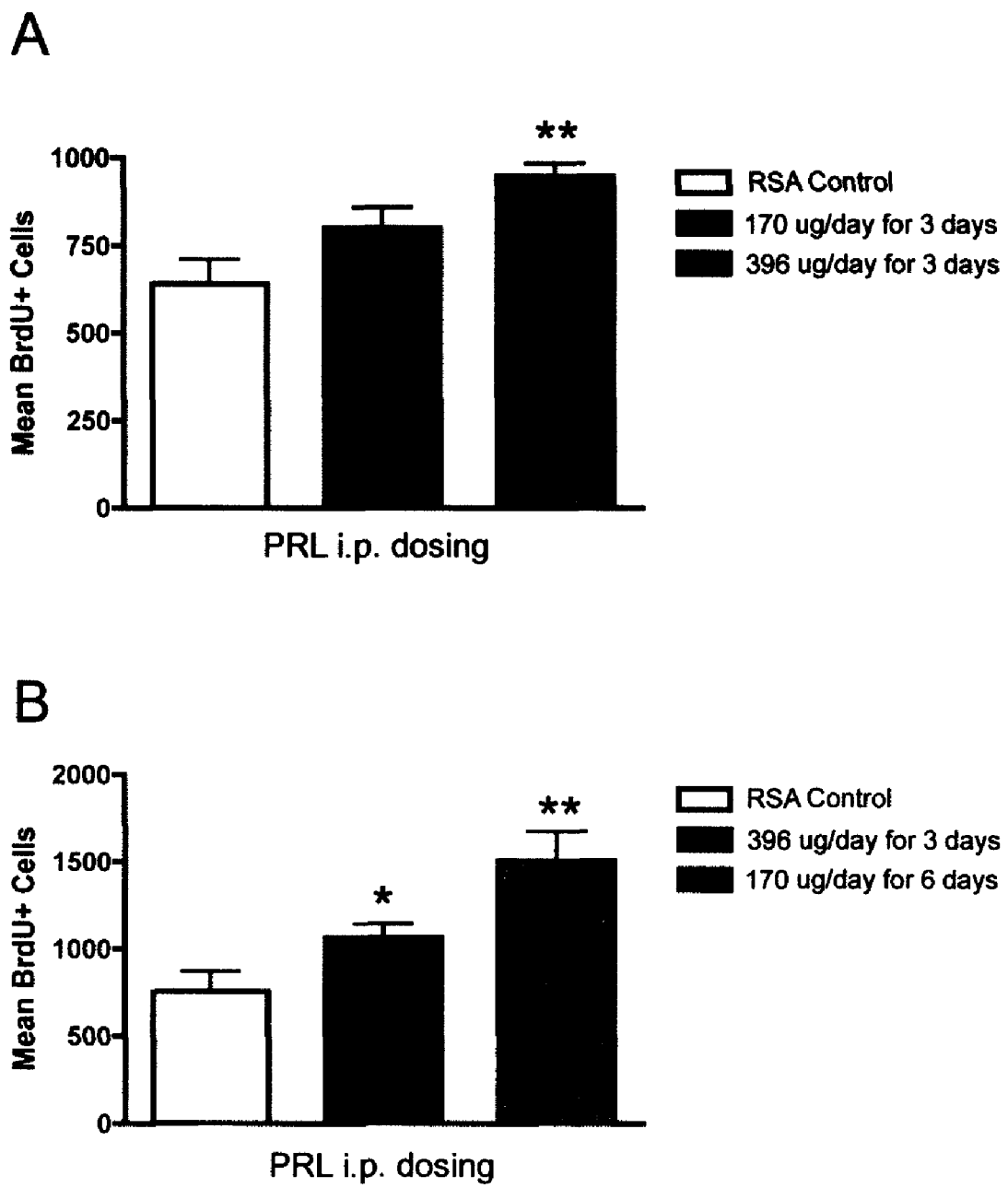

FIG. 2. Prolactin dosing in male rats using single daily intraperitoneal injections. The total number of BrdU+ cells per section are presented for each dosing regime. (A) A small increase in SVZ proliferation was observed with high 3 day doses. (B) The most robust dosing condition for increasing SVZ proliferation levels used a low, 170 μg/day dose each day over 6 days. Significance is relative to RSA control. n=3; *p<0.05; **p<0.01; one-way ANOVA followed by a Tukey posthoc test.

Figure 3:
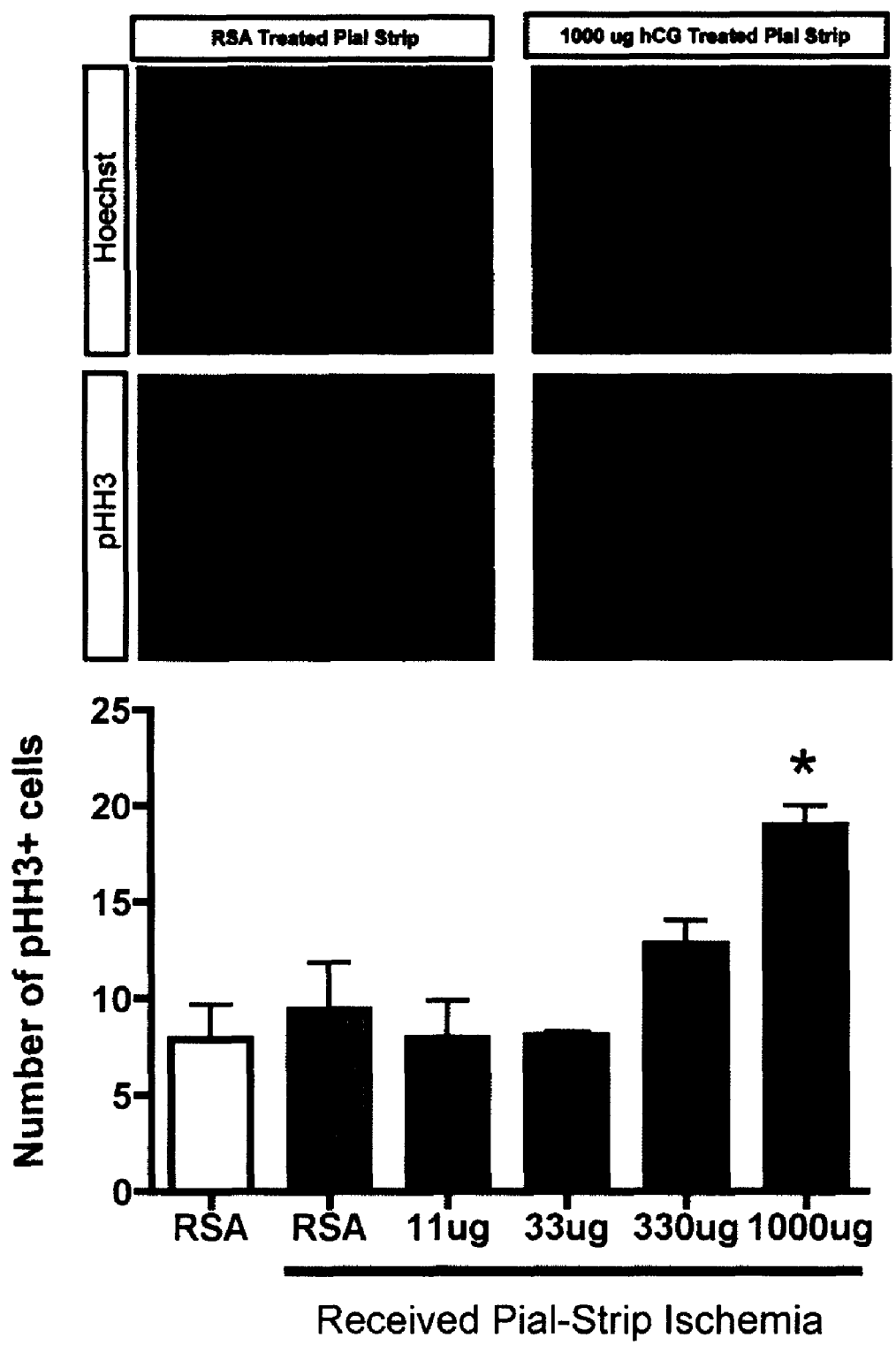

FIG. 3. Single intramuscular injections of hCG on days 1, 3, and 5 post-stroke (stroke=day 0) trigger significantly increased proliferation in the forebrain SVZ. Significant increases in the number of Phospho-Histone H3 positive (pHH3+) cells per ventricle were observed in the 1000 μg dose condition (n=3; *p<0.05; one way ANOVA with Tukey posthoc). Images show the nuclear label Hoechst and pHH3 expression in the dorsolateral corner of the lateral ventricles in RSA pial strip control rats versus 1000 μg hCG dosed animals, note the increase in total cell number and pHH3 expression in SVZ of 1000 μg dosed animals.

Figure 4:
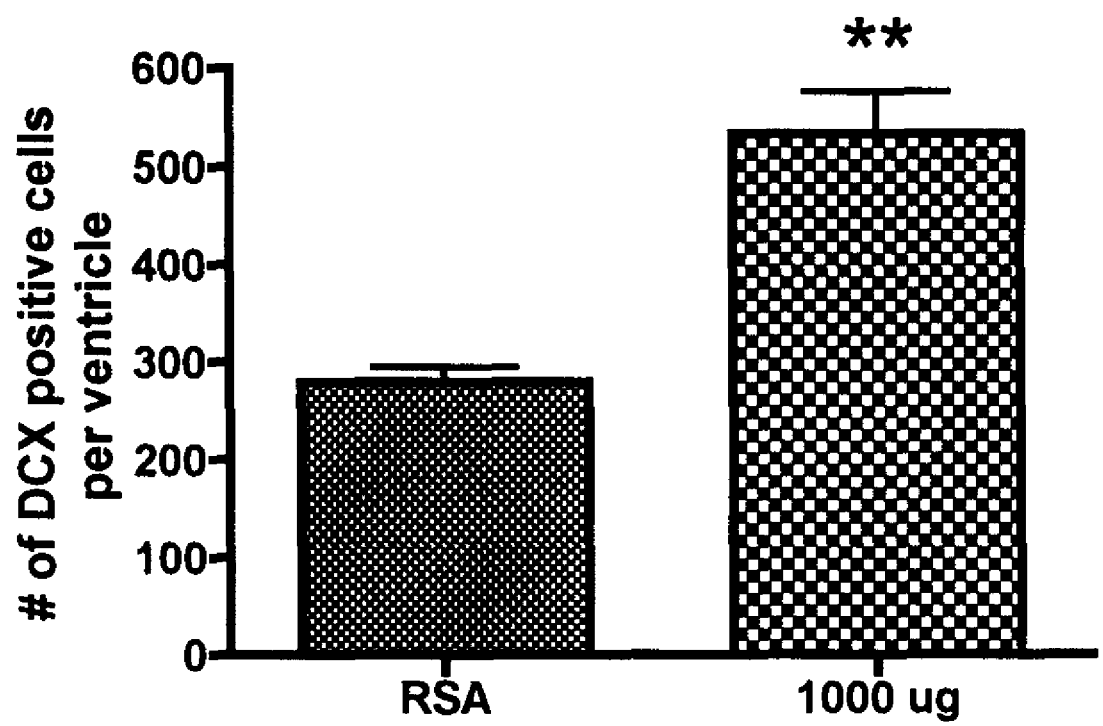

FIG. 4. Single intramuscular injections of 1000 μg per day of hCG on days 1, 3, and 5 post-stroke (stroke=day 0) trigger increased neurogenesis in the forebrain SVZ. The number of doublecortin+ neurons was quantified in the dosed animals and was doubled in the 1000 μg dose animals. (n=3; **p<0.01)

Figure 5:
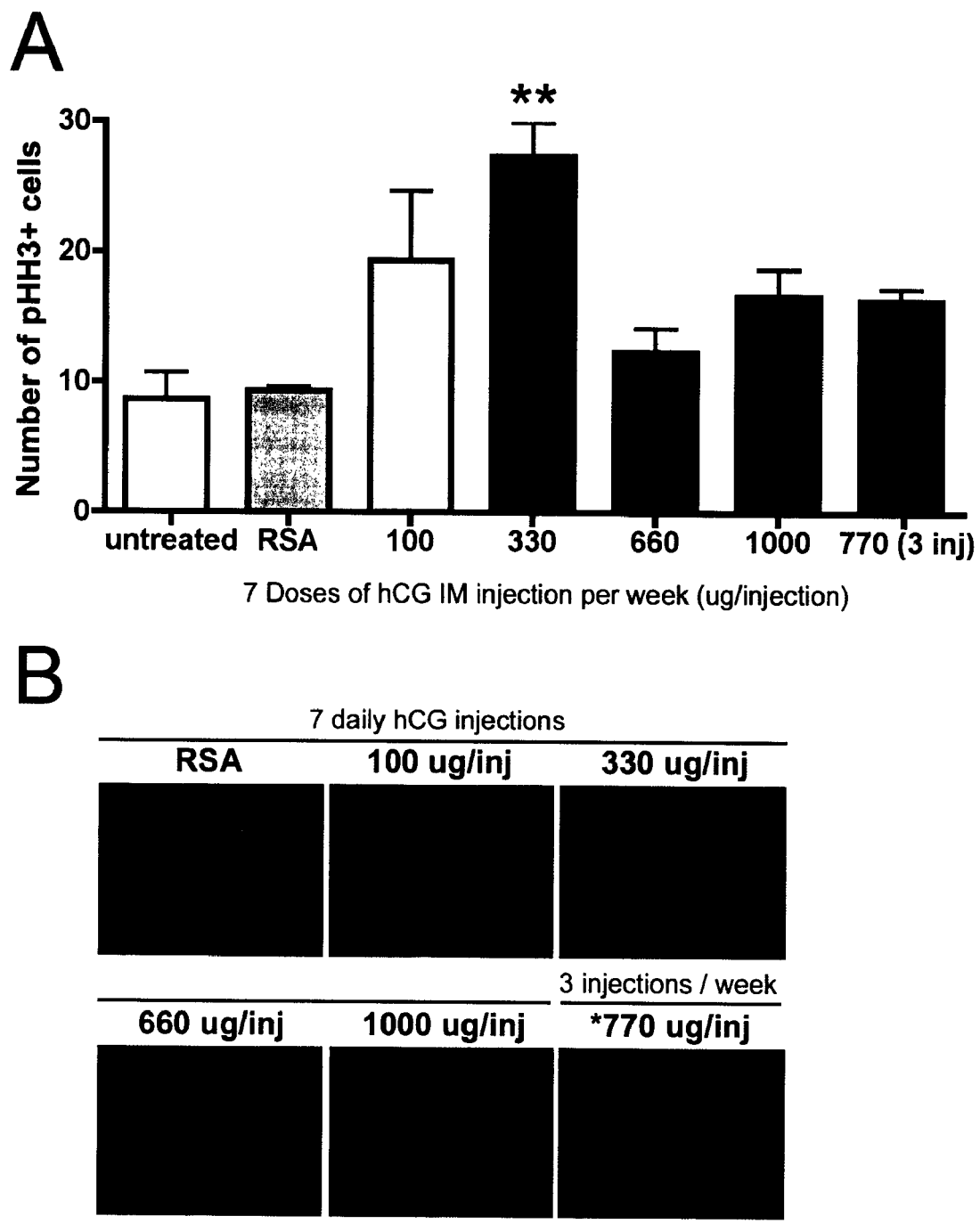

FIG. 5. Single intramuscular injections of hCG given daily for 7 days starting 24 hrs post-stroke (stroke=day 0). (A) The daily 330 μg/injection dosing regime significantly increased the number of proliferating (pHH3+ cells) in the SVZ relative to all other dosing conditions and controls (n=3; *p<0.01; one way ANOVA with Tukey posthoc). (B) Observation of the ischemic lesions in the motor cortex of dosed rats revealed that animals receiving the 330 μg/injection daily dosing regime demonstrated new tissue growth and filling in of the lesion site with a tissue plug.

Figure 6:
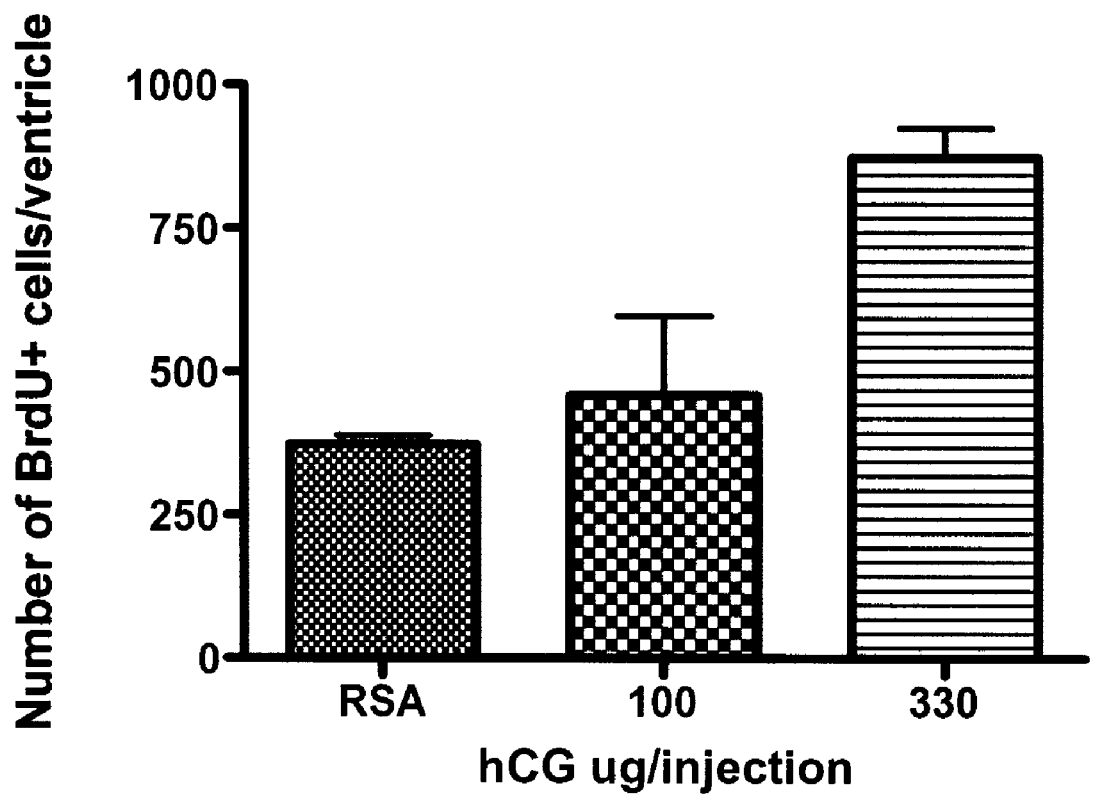

FIG. 6. Increased proliferation in the SVZ of 330 μg/injection daily hCG dosed animals confirmed by counts of BrdU+ cells. The number of BrdU+ cells per ventricle was significantly increased in the 330 μg/injection condition relative to control and 100 μg/injection (p<0.01; n=3; one way ANOVA with Tukey posthoc analysis). These results further confirmed the increase in proliferation observed with pHH3 staining.

Like reference symbols in the various drawings indicate like elements.

DETAILED DESCRIPTION

Currently there are no neural stem cell proliferating and differentiating agents that have been clinically approved for use in treatment of neurological diseases or conditions. These agents are useful in treating neurological diseases and conditions, thus there is a need for effective dosing regimens using these agents. Effective dosing regimens for neural stem cell proliferating agents, kits comprising effective dosing regimens for neural stem cell proliferating agents, and uses thereof are provided herein. In particular, neural stem cell proliferating agents are delivered to mammalian subjects at a low dose in a continuous fashion, as opposed to the administration of a high-dose in a short period of time. For example, for a given total effective dose, a dosing regimen comprising daily delivery of ⅙ of the total amount for six days was more effective than delivering ⅓ of the total amount daily for three days.

Prior to describing the methods and kits in further detail, the terms used in this application are defined as follows unless otherwise indicated. The headings herein are for organizational purposes only and are not meant to limit the description provided herein or the claims attached hereto.

Definitions

A neural stem cell or NSC is a stem cell in the neural cell lineage. A stem cell is a cell which is capable of reproducing itself. In other words, daughter cells which result from stem cell divisions include stem cells. The neural stem cells are capable of ultimately differentiating into all the cell types in the neural cell lineage, including neurons, astrocytes and oligodendrocytes (astrocytes and oligodendrocytes are collectively called glia or glial cells). Thus, the neural stem cells referred to herein are multipotent neural stem cells.

A neural stem cell proliferating agent is a substance that is capable of increasing the number of neural stem cells, for example, by stimulating proliferation, inhibiting differentiation, and/or preventing death of neural stem cells.

A neural stem cell differentiating agent is a substance capable of selectively enhancing neuron formation or glial cell formation.

To deliver or administer a substance continuously to a subject means to deliver or administer the substance at least once per day or up to throughout the day on consecutive days, for a period of time. For example, the substance may be administered systemically by injection (e.g., IM or subcutaneously) or taken orally daily at least once per day, or administered by infusion in a manner that results in the daily delivery into the tissue or blood stream of the subject. Optionally, the substance is delivered by infusion or a means other than infusion. As used herein the term systemically does not include intracerebral ventricular infusion. The duration in which the substance is continuously delivered or administered can last from three days to several years, even for the rest of a subject's life. For example, the duration may be 3-6 days, 3-14 days, 3-21 days, 3-28 days, 1-4 months, 1-6 months, 1-9 months, 1-12 months, 1-2 years, 1-3 years, 1-5 years, 1-10 years, and the like. For further example the treatment period for continuous delivery can be at least about three days, at least about four days, at least about five days, at least about six days, at least about seven days, or at least about fourteen days. Further, the substance can be delivered consecutively on days 1, 2, and 3 of the administration period.

A neurodegenerative disease or condition is a disease or medical condition associated with neuron loss or dysfunction. Examples of neurodegenerative diseases or conditions include neurodegenerative diseases, central nervous system injuries or dysfunctions. Neurodegenerative diseases include, for example, Alzheimer's disease or other dementia, multiple sclerosis (MS), schizophrenia, macular degeneration, glaucoma, diabetic retinopathy, peripheral neuropathy, Huntington's disease, amyotrophic lateral sclerosis, and Parkinson's disease. CNS injuries include, for example, cerebrovascular events like strokes (e.g., hemorrhagic strokes, focal ischemic strokes or global ischemic strokes), ocular ischemia, and dural sinus thrombosis; traumatic brain or spinal cord injuries (e.g., injuries caused by a brain or spinal cord surgery or physical accidents); concussion; injury induced by drugs, (e.g., chemotherapeutics, recreational drugs, and neuroleptics); coronary artery bypass graft (CABG) surgery; and ischemia at child birth. CNS dysfunctions include, for example, depression, epilepsy, neurosis and psychosis. Examples of neurodegenerative conditions include aging. The number of neural stem cells in the subventricular zone is significantly reduced in aged mice. Accordingly, amelioration of neurologic problems associated with aging is achieved by administering neural stem cell proliferating agents and, optionally, neural stem cell differentiating agents according to the methods and kits.

Treating and ameliorating mean the reduction or complete removal of one or more symptoms of a disease or medical condition. Such treatment or amelioration can include the delay or elimination of the onset of one or more symptoms when administered to a person at risk for the disease or medical condition.

A polypeptide which shares substantial sequence similarity with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level. Thus, substantial similarity can constitute about 30-99% identity.

The phrase percent identity or % identity of an analog or variant with a native factor refers to the percentage of amino acid sequence in the native factor which are also found in the analog or variant when the two sequences are aligned. Percent identity can be determined by any methods or algorithms established in the art, such as LALIGN or BLAST.

A polypeptide possesses a biological activity of a native factor if it is capable of binding to the receptor for the native factor or being recognized by a polyclonal antibody raised against the native factor. Preferably, the polypeptide is capable of specifically binding to the receptor for the native factor in a receptor binding assay.

A functional agonist of a native factor is a compound that binds to and activates the receptor of the native factor, although it does not necessarily share a substantial sequence similarity with the native factor.

A lutenizing hormone or LH is a protein which (1) comprises a polypeptide that shares substantial sequence similarity with a native mammalian LH, preferably the native human LH; and (2) possesses a biological activity of the native mammalian LH. The native mammalian LH is a gonadotropin secreted by the anterior lobe of the pituitary. LH is a heterodimer consisting of non-covalently bound alpha and beta subunits. The alpha subunit is common among LH, FSH and hCG, and the beta subunit is specific for each hormone. The LH useful in the present methods and kits may have the native alpha subunit, with the beta subunit sharing a substantial sequence similarity with a native mammalian LH. Alternatively, the LH may have the native beta subunit, with the alpha subunit sharing a substantial sequence similarity with a native mammalian LH. The LH may also have both the alpha and beta subunit sharing a substantial sequence similarity with a native, corresponding subunit. Thus, the term LH encompasses LH analogs which comprise a deletional, insertional, or substitutional mutants of a native LH subunit. Furthermore, the term LH encompasses the LHs from other species and the naturally occurring variants thereof. In addition, an LH may also be a functional agonist of a native mammalian LH receptor.

A human chorionic gonadotropin or hCG is a protein which (1) comprises a polypeptide that shares substantial sequence similarity with the native hCG; and (2) possesses a biological activity of the native hCG. The native hCG is a heterodimer consisting of non-covalently bound alpha and beta subunits. The alpha subunit is common among LH, FSH and hCG, and the beta subunit is specific for each hormone. However, the beta subunits of hCG and LH share an 85% sequence similarity. The hCG useful in the present methods and kits may have the native alpha subunit, with the beta subunit sharing a substantial sequence similarity with the native hCG. Alternatively, the hCG may have the native beta subunit, with the alpha subunit sharing a substantial sequence similarity with the native hCG. The hCG may also have both the alpha and beta subunit sharing a substantial sequence similarity with the native, corresponding subunit. Thus, the term hCG encompasses hCG analogs which comprise a deletional, insertional, or substitutional mutants of a native hCG subunit. Furthermore, the term hCG encompasses the hCG counterparts from other species and the naturally occurring variants thereof. In addition, an hCG may also be a functional agonist of a native mammalian hCG/LH receptor.

A prolactin is a polypeptide which (1) shares substantial sequence similarity with a native mammalian prolactin, preferably the native human prolactin; and (2) possesses a biological activity of the native mammalian prolactin. The native human prolactin is a 199 amino acid polypeptide synthesized mainly in the pituitary gland. Thus, the term prolactin encompasses prolactin analogs which are the deletional, insertional, or substitutional mutants of the native prolactin. Furthermore, the term prolactin encompasses the prolactins from other species and the naturally occurring variants thereof.

In addition, a prolactin may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode et al., 1996); or a ligand for the prolactin receptor as described in U.S. Pat. Nos. 5,506,107 and 5,837,460.

An epidermal growth factor or EGF means a native EGF or any EGF analog or variant that shares a substantial amino acid sequence similarity with a native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51 gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

In addition, an EGF may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, 1985 and U.S. Pat. No. 5,723,115).

A pituitary adenylate cyclase activating polypeptide or PACAP means a native PACAP or any PACAP analog or variant that shares a substantial amino acid sequence similarity with a native PACAP, as well as at least one biological activity with the native PACAP, such as binding to the PACAP receptor. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

In addition, a PACAP may also be a functional agonist of a native mammalian PACAP receptor. For example, the functional agonist may be maxadilan, a polypeptide that acts as a specific agonist of the PACAP type-1 receptor (Moro et al., 1997).

An erythropoietin or EPO means a native EPO or any EPO analog or variant that shares a substantial amino acid sequence similarity with a native EPO, as well as at least one biological activity with the native EPO, such as binding to the EPO receptor. Erythropoietin analogs and variants are disclosed, for example, in U.S. Pat. Nos. 6,048,971 and 5,614,184.

In addition, an EPO may also be a functional agonist of a native mammalian EPO receptor. For example, the functional agonist may be EPO mimetic peptide 1 (EMP1; Johnson et al., 2000); one of the short peptide mimetics of EPO as described in Wrighton et al., 1996 and U.S. Pat. No. 5,773,569; any small molecular EPO mimetic as disclosed in Kaushansky, 2001; an antibody that activates the EPO receptor as described in U.S. Pat. No. 5,885,574, WO 96/40231, WO 97/48729, Fernandez-Pol, 1985 or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952), or a ligand for the EPO receptor as described in U.S. Pat. Nos. 5,506,107 and 5,837,460.

A LH/hCG-inducing agent is a substance that, when given to an animal, is capable of increasing the amount of LH or hCG in the animal. For example, LH releasing hormone (LHRH) stimulates the secretion of LH.

A pheromone is a substance that serves as a signal to another animal of the same species, usually of the opposite gender. A mammalian pheromone can be a protein or a small molecule. Preferably, the pheromone is selected from the group consisting of 2-sec-butyl-4,5-dihydrothiazole (SBT), 2,3-dehydro-exo-brevicomin (DHB), alpha and beta framesenes, 6-hydroxy-6-methyl-3-heptanone, 2-heptanone, trans-5-hepten-2-one, trans-4-hepten-2-one, n-pentyl acetate, cis-2-penten-1-yl-acetate, 2,5-dimethylpyrazine, dodecyl propionate, and (Z)-7-dodecen-1-yl acetate (see, e.g., Dulac et al., 2003).

An effective amount is an amount of a therapeutic agent sufficient to achieve the intended purpose. For example, an effective amount of an LH or hCG to increase the number of neural stem cells is an amount sufficient, in vivo or in vitro, as the case may be, to result in an increase in neural stem cell number. An effective amount of an LH or hCG to treat or ameliorate a neurodegenerative disease or condition is an amount of the LH/hCG sufficient to reduce or remove one or more symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

An equipotent amount of a neural stem cell proliferating agent is the amount of a neural stem cell proliferating agent required to obtain the same or equivalent effect as another neural stem cell proliferating agent. Equipotent amounts can be specified by a relative level or result of an equipotent amount. Thus, an equipotent amount or dose could be the amount or dose of a neural stem cell proliferating agent required to obtain the same level in blood serum or cerebral spinal fluid as another, specific neural stem cell proliferating agent.

A drug delivery device is an object suitable for administration of an effective amount of a neural stem cell proliferating agent or a differentiating agent. A drug delivery device can effect administration of neural stem cell proliferating agent or a differentiating agent by any method established in the art, including, for example, intravenous, intra-arterial, intracolonical, intratracheal, intraperitoneal, intranasal, intravascular, intrathecal, intracranial, intramarrow, intrapleural, intradermal, subcutaneous, intramuscular, intraperitoneal, oral, topical administration, pulmonary administration, or any combination thereof. A drug delivery device can be an implantable device or a pump, including, for example, an osmotic pump. Optionally, the drug delivery device is an infusion device or component thereof or, alternatively, is a device for other means than infusion.

Continuous Delivery

To improve the dosing regimen for prolactin, various amounts of prolactin were administered to rats daily for 6 days and the effects on neural stem cell numbers were examined (Example 1). The results show that 170 µg/day was the optimal amount in this dosing schedule. This dosing regimen, 170 µg/day for 6 days, was then varied by shortening the dosing period (170 µg/day for 3 days) or combining a higher daily dose with a shortened period to achieve a similar total dose (396 µg/day for 3 days). The results indicate that the continuous delivery of a lower dose over a longer period time is more effective than the combination of higher dose and shorter delivery time.

Accordingly, provided herein is a method for optimizing the efficacy of an effective amount of a neural stem cell proliferating agent in increasing the number of neural stem cells in a mammal, comprising administering the neural stem cell proliferating agent to the mammal continuously for a period of time, wherein the total dosage of the neural stem cell proliferating agent administered in said period of time equals the effective amount, and wherein said period of time is at least three days.

A method for optimizing the efficacy of an effective amount of a neural stem cell proliferating agent in treating or ameliorating a neurodegenerative disease in a mammal is provided, wherein the method comprises administering the neural stem cell proliferating agent to the mammal continuously for a period of time, wherein the total dosage of the neural stem cell proliferating agent administered in said period of time equals the effective amount, and wherein said period of time is at least three days.

A method for treating or ameliorating a neurodegenerative disease in a mammal is also provided, comprising administering an effective amount of a neural stem cell proliferating agent to the mammal continuously for a period of time, wherein said period of time is at least three days.

Additionally provided herein is a further method for treating or ameliorating a neurodegenerative disease or condition in a mammal. This method comprises administering to the mammal a neural stem cell proliferating agent and a neural stem cell differentiating agent, wherein the neural stem cell proliferating agent is administered continuously at least three times systemically over a first treatment period and wherein the neural stem cell differentiating agent is administered over a second treatment period.

The methods provided herein, for example, can use the proliferating agents prolactin, hCG, LH, G-CSF, GM-CSF, pheromones, or VEGF for treatment of a neurodegenerative disease or condition through administration of an effective amount of the proliferating agent to the subject with a neurodegenerative disease or condition. By way of example, the proliferating agents hCG and LH bind the same receptor, and can be used interchangeably in equipotent doses in the specific examples provided herein. As a further example, the proliferating agent hCG can be administered intramuscularly (IM) at a dose of about 120-200 IU/kg/day followed by intravenous (IV) administration of about 570-950 IU/kg/day of EPO. For further example, an hCG can be intramuscularly administered at a dose of 160 IU/kg/day followed by intravenous administration of 765 IU/kg/day of EPO. Such administration of a neural stem cell stimulating agent can be followed by several days of administration of a differentiating agent such as EPO. Equipotent doses of other neural stem cell proliferating agents can also be used in similar regimens.

Also provided herein is a kit for providing an effective amount of a neural stem cell proliferating agent, comprising a dosage of said neural stem cell proliferating agent for use over a treating period, wherein the total dosage of the neural stem cell proliferating agent administered in said treating period equals the effective amount, and wherein said treating period is at least three days, and instructions for use of the kit.

The kit can further provide a dosage of a differentiating agent for use over a treating period, wherein the total dosage of the differentiating agent administered in said treating period equals the effective amount, and wherein said treating period is at least three days.

The total dosage of each of the neural stem cell proliferating agent, differentiating agent, or other agents in the kit can be provided in one container, a plurality of containers, or any combination thereof. For example, the total dosage for the neural stem cell proliferating agent or agents can be in one container suitable for providing a metered dose or suitable for extraction of a dose for example, by the person to be treated or by another person, such as a caregiver. Instead of a single container, the neural stem cell proliferating agent or agents can be present in a plurality of containers that provide aliquots for doses suitable for administration daily, weekly, month, or the like. A single container or a plurality of containers for the differentiating agent or other agents can similarly be provided in the kit. Combinations may also be included whereby one container of neural stem cell proliferating agent(s) but a plurality of differentiating agent(s) containers or the opposite may be included in the kit. Also, the total dosage of a neural stem proliferating factor for a first treating period may be in a single container or a plurality of containers, the total dosage for a second treating period may be in a single container or a plurality of containers, or any combination thereof.

The kit can further comprise a device or means for monitoring hematocrit levels in a patient or a suitable device for removing an amount of blood from the patient or both a monitor and a blood sampling device. Blood sampling and monitoring is desirable because hematocrit levels may rise above acceptable levels. Acceptable hematocrit levels can be determined by any standard established in the art.

The kit is suitable for use in a health care facility such as an inpatient care facility or an emergency care facility. A health care facility includes, for example, a hospital. The kit is also suitable for use after discharge from or without admission in an the inpatient care facility. Packaging in the form of a kit advantageously facilitates early release of patients from a health care facility by permitting patient treatment at a long term care facility or at home, for example, by self-treatment, outpatient treatment, or treatments by a caregiver or health care provider in a home, a long term care facility, or the like.

In the methods and kits, the period of time (i.e., the treating period) may be, for example, at least about three, four, five, six, seven, eight, nine, ten, eleven, twelve, fourteen, twenty-one, twenty-eight days, or any number of days between about 3 and about 28. Optionally, the methods and kits may comprise administering to the mammal the neural stem cell proliferating agent continuously in a second treating period, wherein the second treating period starts after the end of the period of time, and wherein the second treating period is at least three days. The second treating period, like the first treating period, may be, for example, at least about three, four, five, six, seven, eight, nine, ten, eleven, twelve, fourteen, twenty-one, or twenty-eight days. The interval between the first treating period and the next treating period may also be, for example, at least about one, two, three, four, five, six, seven, eight, nine, ten, eleven, twelve, fourteen, twenty-one, or twenty-eight days. This treating schedule can be repeated several times or many times. The neural stem cell proliferating agent used in the second or subsequent treating period may be the same as or different than the neural stem cell proliferating agent used in the first treating period or used in other treating periods. Furthermore, more than one neural stem cell proliferating agent may be used in a single treating period. Thus, kits useful in the methods may contain one or more neural stem cell proliferating agent for one or more treating periods.

The neural stem cell proliferating agent can be administered by any method established in the art, such as by intravenous, intra-arterial, intracolonical, intratracheal, intraperitoneal, intranasal, intravascular, intrathecal, intracranial, intramarrow, intrapleural, intradermal, subcutaneous, intramuscular, oral, topical administration, pulmonary administration, or any combination thereof. Optionally, a drug delivery device or component thereof for administration can be included in a kit containing the neural stem cell proliferating agent.

The methods described herein can also include monitoring levels of the neural stem cell proliferating agent or neural stem cell differentiating agent in a biological fluid of the mammal. The biological fluid monitored can be, for example, cerebral spinal fluid or blood. For example, the level of hCG (or another neural stem cell proliferating agent or neural stem cell differentiating agent) in blood serum can be measured after administration either during or after a treatment period. Equipotent levels of various neural stem cell proliferating agent or neural stem cell differentiating agent can be both determined and monitored in biological fluid.

Specific dosage units (i.e., the amount or a single administration within a series of administrations in a treatment period) can be specified for a neural stem cell proliferating or differentiating agents to be used with the methods disclosed herein. These dosage units can be within the specific dosages and dosage ranges specified herein. Dosage units can be defined with respect to the amount that must be administered to achieve a desired level of a neural stem cell proliferating or differentiating agent in a subject. For example, a dosage unit of a neural stem cell proliferating agent that provides a neural stem cell proliferating or differentiating agent level in blood serum of 0.03 IU/L to 5,000,000 IU/L. Or, as a further example, a dosage unit of a neural stem cell proliferating or differentiating agent that provides a proliferating agent level in cerebral spinal fluid of about 0.003 IU/L to about 5,000 IU/L.

In the methods and in the instructions for the kits, the neural stem cell proliferating agent is delivered systemically, more preferably by systemic administration at least once per day. In some embodiments, the neural stem cell proliferating agent is not delivered by infusion.

The neural stem cell proliferating agent may be any substance that is capable of increasing the number of mammalian neural stem cells, in vivo and in vitro. As used herein a promoting agent has the same meaning as a proliferating agent. Agents that can increase neural stem cell number include, but are not limited to:

1. Follicle-stimulating hormone (FSH), which often acts in concert with LH and induces LH receptor expression, thereby enhancing the effects of LH signaling.
2. Growth hormone (GH), which can stimulate neural stem cell proliferation.
3. Insulin growth factors (IGFs), including IGF-1, which are somatomedians that are released from many tissues in response to GH and mediate many of the growth proliferating effects of GH and which stimulate neural stem cell proliferation.
4. Growth hormone releasing hormone (GHRH), which is secreted from the hypothalamus and induces GH release from the anterior pituitary, resulting in increased levels of circulating GH.
5. Prolactin (PRL), which is secreted from the anterior pituitary and which is promotes neural stem cell proliferation.
6. Prolactin releasing peptide (PRP), which triggers the release of prolactin.
7. Fibroblast growth factor (FGF), a mitogenic agent for neural stem cells.
8. Estrogen, which promotes the proliferation of neural stem cells, including for example in the hippocampus.
9. Serotonin, which promotes the proliferation of neural stem cells in the hippocampus.
10. Epidermal growth factor (EGF), a mitogenic agent for neural stem cells.
11. Transforming growth factor alpha (TGFα), a mitogenic agent for neural stem cells.
12. Gonadotropin releasing hormone (GnRH), which triggers the release of LH.
13. Ciliary neurotrophic factor (CNTF) and leukemia inhibitory factor (LIF) which signal via the gp130 subunit by a signaling pathway that promotes neural stem cell self-renewal, thereby expanding the neural stem cell population of the brain.
14. Granulocyte colony stimulating factor (G-CSF).
15. Granulocyte-macrophage colony stimulating factor (GM-CSF).
16. Vascular endothelial growth factor (VEGF).
17. Lutenizing hormone (LH).
18. Human chorionic gonadotropin (hCG).
19. Pheromones.

Furthermore, differentiating agents can be administered to selectively enhance neuron formation or glial cell formation. These differentiating agents can also be delivered according to the dosing regimens and kits. Exemplary differentiating agents include, but are not limited to:

1. Erythropoietin (EPO), which enhances neural stem cell commitment to neuronal cell lineage and is useful for treating mouse and rat models of stroke.
2. Brain derived neurotrophic factor (BDNF), which is a known survival factor and differentiating agent that promotes the neuronal lineage.
3, Transforming growth factor beta and bone morphogenetic proteins (BMPs), which are differentiating agents that promote the neuronal lineage and the generation of specific neuronal phenotypes (e.g., sensory interneurons in the spinal cord).
4. Thyroid hormone (TH, including both the T3 and T4 forms), a differentiating agent that promotes the maturation and generation of oligodendroctyes. See, e.g., Rodriguez-Pena, 1999.
5. Thyroid stimulating hormone (TSH) and Thyroid releasing hormone (TRH), which promote the release of TH from the anterior pituitary resulting in increased levels of circulating TH. This agent could be used in combination with LH or hCG to promote oligodendrogliogenesis from neural stem cells.
6. Sonic hedgehog (SHH), a morphogen that patterns the developing CNS during development and, in different concentrations, promotes the generation of specific types of neurons (e.g., motor neurons in the spinal cord) and oligodendrocytes. This agent could be used in combination with LH or hCG to promote neurogenesis and/or oligodendrogliogenesis from neural stem cells.
7. Platelet derived growth factor (PDGF), which promotes the generation and differentiation of oligodendrocytes from neural stem cells. This agent could be used in combination with LH or hCG to promote oligodendrogliogenesis from neural stem cells.
8. Cyclic AMP and agents which enhance the cAMP pathway, such as pituitary adenylate cyclase activating polypeptide (PACAP) and serotonin, which selectively promote neuron production.

Any of the methods and kits can comprise a plurality of neural stem cell proliferating agents and/or neural cell differentiating agents. Thus, one or more neural stem cell proliferating agents can be administered together or sequentially and can be administered via separate compositions or in combination within a single composition. Further, one or more neural stem cell proliferating agents and one or more neural stem cell differentiating agents can be administered together or sequentially and can be administered via separate compositions or in combination within a single composition. For example, PRL and LH or hCG can be used in combination to maximize neural stem cell proliferation; PRP can be used in combination with LH or hCG to maximize neural stem cell proliferation; GnRH can be used in combination with or in place of LH or hCG to increase circulating levels of LH and enhance neural stem cell proliferation; and CNTF and LIF can be used in combination with LH or hCG to promote neural stem cell proliferation and increase the size of the neural stem cell population within the CNS. Further for example, prolactin can be used with EPO, LH can be used with EPO, and hCG can be used with EPO. All other combinations, not explicitly set forth, can also be used.

Appropriate dosages for the factors can be determined according to established methods in the art. For example, the dosage for prolactin may range from about 0.510 IU/kg/day to about 100,000 IU/kg/day, such as, for example, about 0.510-90,000; 0.510-75,000; 0.510-50,000; 0.510-25,000; 0.510-10,000; 100-5,000; 100-2,000; 500-2,000; 1,000-2,000; 100-1,000; 200-800 IU/kg/day. The dosage for hCG can range from about 0.5 IU/kg/day to about 3,000,000 IU/kg/day, such as, for example, about 0.5-2,000,000; 0.5-1,000,000; 0.5-500,000; 0.5-250,000; 0.5-100,000; 0.5-50,000; 10-25,000; 10-10,000; 240-216,000; 1,200-2,000; 2,160; or 1,600 IU/kg/day. hCG can also be provided at a dose of 10,000 IU/day. The dosage for LH can range from about 0.5 IU/kg/day to about 500,000 IU/kg/day, such as, for example, about 0.5-300,000; 0.5-200,000; 0.5-100,000; 0.5-50,000; 0.5-25,000; 24-21,600; 1,000; 120-200; 216; or 160 IU/kg/ day. LH can also be provided at a dose of 10,000 IU/day. The dosage for EPO can range from about 100 IU/kg/day to about 2000 IU/kg/day, such as, for example, about 100-1500; 100-1000; 160-1000; 570-950; 765; or 1020 IU/kg/day. EPO can also be provided at a dose of about 30,000 IU/day. Equipotent doses of other agents can be used. Unless otherwise specified, the dosage here refers to the average dose delivered per day.

The neural stem cell proliferating agent and the differentiating agent can optionally be packaged in a kit, such that the total amount of the neural stem cell proliferating agent and the differentiating agent to be delivered during the treating period is contained in the kit. The kit can optionally contain other components or combinations of other components, including for example a blood sampling device or a component thereof.

The differentiating agent can be administered by any method established in the art, such as by intravenous, intraarterial, intracolonical, intratracheal, intraperitoneal, intranasal, intravascular, intrathecal, intracranial, intramarrow, intrapleural, intradermal, subcutaneous, intramuscular, oral, topical administration, or any combination thereof. Optionally, a drug delivery device for administration can be included in a kit containing the differentiating agent.

The neural stem cell proliferating agent can be administered to the mammal within about 14 days (e.g., 0 to about 14 days) of a central nervous system (CNS) injury, onset of symptoms, or diagnosis. As used herein 0 days refers to the time of CNS injury, onset of symptoms, or diagnosis. Optionally, the neural stem cell proliferating agent can be administered at least about 13, 12, 11, 10, 9, 8, 7, 6, 5, 4, 3, 2, or 1 day(s) (e.g., 0 to about 5 days) after a CNS injury, onset of symptoms, or diagnosis. Optionally, the neural stem cell proliferating agent can be administered to the mammal within about 24 hours of a CNS injury, onset of symptoms, or diagnosis. Optionally, the neural stem cell proliferating agent can be administered to the mammal within about 12, 11, 10, 9, 8, 7, 6, 5, 4, 3, 2, 1 hour(s) of a CNS injury, onset of symptoms, or diagnosis.

A mammal treated using the methods and kits described herein can be of any age, including a child, juvenile or an adult.

EXAMPLES

In the examples below, the following abbreviations have the following meanings. Abbreviations not defined have their generally accepted meanings.
° C.=degree Celsius
hr=hour
min=minute
µM=micromolar
mM=millimolar
M=molar ml milliliter
µl=microliter
mg=milligram
µg=microgram
FBS=fetal bovine serum
PBS=phosphate buffered saline
DMEM=Dulbecco's modified Eagle's medium
MEM=modified Eagle's medium
EGF=epidermal growth factor
NSC=neural stem cell
SVZ=subventricular zone
PACAP=pituitary adenylate cyclase activating polypeptide
BMP=bone morphogenetic protein
RSA=rat serum albumin

Example 1

Continuous Administration of Prolactin

Male rats (250-300 g) were used in two prolactin dosing experiments. Prolactin was given by subcutaneous mini-osmotic pump infusions (Alzet minipumps)—one injection daily. Stock prolactin was diluted in bicarbonate buffer and the stock was further diluted in 1 mg/ml Rat Serum Albumin (RSA) in saline for injections. The rats did not receive ischemic injuries. On the $6^{th}$ day the animals received 6 BrdU injections (Sigma-Aldrich) (60 mg/kg, i.p.) over 10 hrs and were sacrificed 30 min following the final BrdU injection. The brains were cryosectioned and BrdU+ cells were quantified in the SVZ using 8 sections per animal. The results are presented as total number of BrdU+ cells in the SVZ or as an average per section as indicated in the figure legend.

Experiment #1:

Rats were dosed for 6 days and received subcutaneous infusions of RSA (control) or rat prolactin (National Hormone and Peptide Program, Torrance, Calif.) at the following doses (3 rats in each group):
  *10×=99 ul/pump(2 mg/0.25 ml PRL)–113 µg/day
  **15×=148.5 ul/pump(2 mg/0.25 ml PRL)–170 µg/day
  ***20×=198 ul/pump(2 mg/0.25 ml PRL)–226 µg/day
    wherein
  *10×=10 times the dose given for intracerebroventricular infusions (approx 11 µg/day).
  **15×=15 times the dose given for intracerebroventricular infusions.
  ***20×=20 times the dose given for intracerebroventricular infusions.

Figure 1:
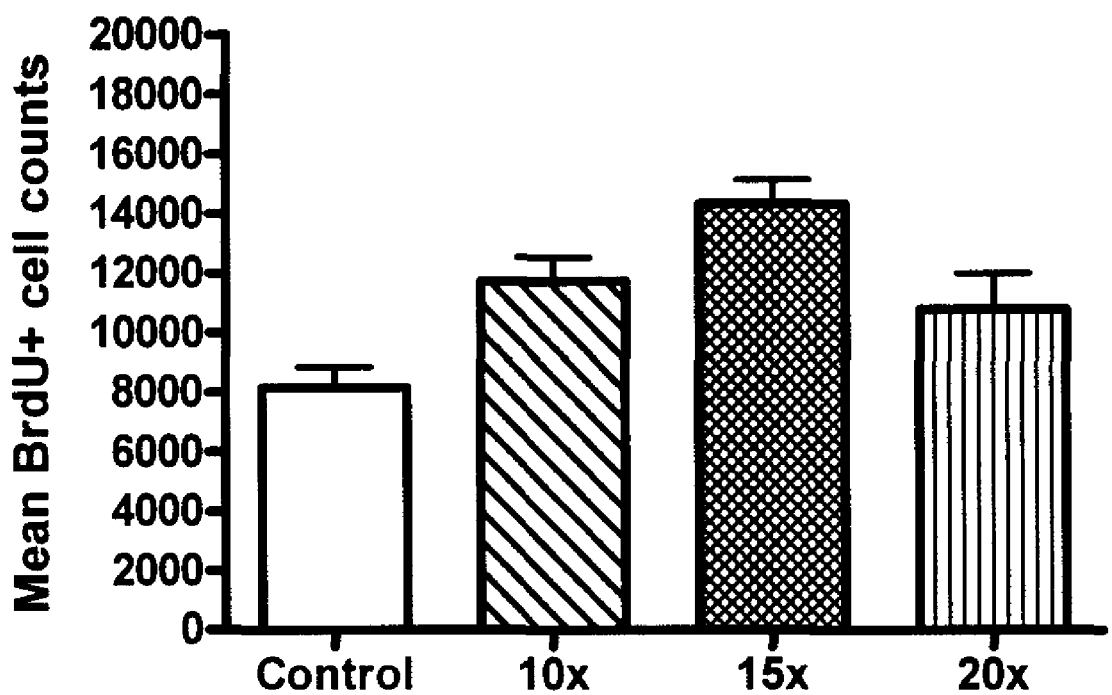
FIG. 1. Six day subcutaneous prolactin infusions in male rats at 10, 15, and 20 times the concentrations used for intracerebroventricular infusions. The total number of bromodeoxyuridine positive (BrdU+) cells in the subventricular zone (SVZ) for 8 sections from each animal is presented. The optimal increase in SVZ proliferation levels was observed with the 15 times dose (170 µg/day for 6 days). (10 times=113 µg/day; 20 times=226 µg/day; Control=rat serum albumin only (RSA)). Significance relative to control: 10×=*p<0.05.

Results:

As shown in FIG. 1, 170 µg/day resulted in the largest increase in proliferation (number of BrdU+ cells) within the forebrain SVZ.

Experiment #2:

Rats were dosed for 3 or 6 days and received daily single intraperitoneal injections of RSA or rat prolactin (National Hormone and Peptide Program, Torrance, Calif.) at the following doses (3 rats in each group):
  170 µg/day for 3 days
  396 µg/day for 3 days
  170 µg/day for 6 days Results:

As shown in FIG. 2, 170 µg/day delivered for 6 days resulted in the largest increase in proliferation (number of BrdU+ cells) within the forebrain SVZ.

Example 2

Continuous Administration of hCG

The purpose of this study is to determine the dose of hCG that maximizes cell proliferation in the forebrain germinal zone and tissue regeneration of adult male rats that have received a pial-strip devascularizing ischemic injury to the motor cortex.

Methods

Animals and Surgery 250-300 g male rats received a pial-strip devascularization ischemic injury to the motor cortex as previously described (Gonzalez and Kolb. A comparison of different models of stroke on behaviour and brain morphology. Eur J. Neurosci. 2003. 18(7):1950-1962). With the animals under sodium pentobarbital anesthesia (60 mg/kg), a rectangular hole was drilled into the frontal and parietal bones running from +4 to −2 mm anterior/posterior to the bregma and running laterally from 1.5 to 4.5 mm from midline. The dura was removed and a sterile saline-soaked cotton swab was used to wipe the pia and attached blood vessels from the cortical surface.

Dosing

Beginning one day post-stroke (24 hrs later), animals received a single intramuscular (i.m.) injection of human chorionic gonadotropin. Doses were given as described in Table 1 and were delivered in either three injections over 5 days (dosed on days 1, 3, and 5) or as daily injections over one week and injections were given at 9:00 am each day. Control rats received injections of rat serum albumin in saline (RSA; Sigma, 1 mg/ml). On the day of the final dose animals received 6 BrdU injections over 10 hrs, beginning 30 min after the hCG injection. BrdU (Sigma-Aldrich) was given at a dose of 60 mg/kg, i.p. Animals were transcardially perfused with 4% paraformaldehyde. Brains were dissected, cryoprotected in sucrose and cryosectioned. Brains were cryosectioned at 14 microns in two series of 8 slides each with 8 sections per slide. Immunostaining was performed using rabbit anti-phosphohistone H3 (anti-pHH3; 1:100; Upstate Biotechnologies), Rat anti-BrdU (1:100; Seralab), goat anti-doublecortin (DCX; 1:100; Santa Cruz Biotechnologies). The number of phosphohistone H3 (pHH3—a marker of mitotically-active cells), BrdU, and doublecortin (DCX—a marker of immature neurons) positive cells in the forebrain subventricular zone (SVZ) around the lateral ventricle of each animal was quantified in 8 sections and presented as the average number of positive cells per lateral ventricle.

Statistics

Values are means+ standard error of the mean (SEM). Significance was determined using a one-way ANOVA followed by a Tukey HSD posthoc test ($*p<0.05$; $**p<0.01$). Three animals were included in each group.

Results

The present study examines the ability of intramuscular injections of hCG to promote the proliferation of neural stem cells and progenitor cells residing in the adult forebrain subventricular zone (SVZ) following stroke. Animals underwent pial strip devascularization surgery to induce a focal ischemic injury in the motor cortex and treatments began 24 hrs later. In the high bolus dose strategy, animals received 3 doses of hCG over five days on days 1 (24 hrs post-stroke), 3 and 5 as summarized in Table 1. Animals were sacrificed on day 5 for analysis of the levels of proliferation in the forebrain SVZ. As shown in Table 2 and FIG. 3, this regimen was effective in increasing proliferation compared to stroked animals receiving RSA control injections. At a dose of 1000 µg, proliferation was increased by almost 2.5 fold and, as shown in FIG. 4, the number of newly generated doublecortin positive (DCX+) neurons in the SVZ of these animals was similarly significantly increased.

In another study, animals received daily dosing with hCG as summarized in Table 1 for 7 days, beginning 24 hrs post-stroke, and the animals were given BrdU on day 7 for 10 hrs and then sacrificed. As shown in FIG. 5A, the number of dividing cells in the SVZ, as indicated by pHH3 immunoreactivity, was significantly increased in the 330 µg/injection group relative to all other groups. This increase was confirmed by quantifying the number of BrdU+ cells in the SVZ of these animals relative to RSA controls (FIG. 6). There was a trend level increase in the 100 µg treatment group relative to pial strip RSA controls (FIGS. 5A and 6). Note that the untreated animals in FIG. 5 received no injections and no pial strip stroke. As an internal control, a group received the same total dose as the 330 µg/injection group (see Table 1), but the hCG was given in 3 injections of 770 µg/injection on days 1, 3 and 5 and the animals were sacrificed on day 5. Based on this study, a low, regular dose of hCG given at 330 µg/injection daily was most effective for increasing proliferation in the forebrain SVZ following ischemic damage in the brain.

To determine whether any of the dosing regimes might result in the growth of new cortical tissue we analyzed the lesion site in cortex of hCG treated animals. Tissue regrowth was particularly evident in the low, regular daily dosing regime the 330 µg/injection dosed group of animals (FIG. 5B).

Example 3

Continuous Administration of hCG Followed by EPO

Mammals suffering from a neurodegenerative disease or condition can be treated with three once-daily IM doses of hCG (at 10,000 IU/day) on days 1, 2 and 3 of treatment, followed by a one day wash out period (day 4), followed by three once daily I.V. doses of EPO (at 30,000 IU/day) on days 5, 6, and 7 of a the treatment. The first IM hCG dose can be delivered between 24 and 48 hours after the onset of a neurodegenerative condition such as a moderate-severe stroke event. Patients can be examined at several points during treatment, as well as 6 weeks and 3 months after stroke onset. Baseline assessments can include clinical/safety, neurological, hematological, and vascular status, as well as a brain MRI. Assessments of clinical/safety, neurological, hematological, and vascular status can be repeated at 1 day, 15 days, and 80 days after completing the treatment. A brain MRI can be repeated 80 days after completing the treatment (which will be approximately 90 days after onset or diagnosis of a neurologic disease or condition) for comparison purposes.

Any patents or publications mentioned in the specification are indicative of the level of those skilled in the art to which the invention pertains. These patents and publications are herein incorporated by reference in their entirety to the same extent as if each individual publication was specifically and individually indicated to be incorporated by reference.

The present invention is not limited in scope by the embodiments disclosed in the examples which are intended as illustrations of a few aspects of the invention and any embodiments which are functionally equivalent are within the scope of this invention. Various modifications of the invention in addition to those shown and described herein will become apparent to those skilled in the art and are intended to fall within the scope of the appended claims. Further, while only certain representative combinations of the compositions disclosed herein are specifically discussed in the embodiments above, other combinations of the compositions will become apparent to those skilled in the art and also are intended to fall within the scope of the appended claims. Thus a combination of steps or compositions may be explicitly mentioned herein; however, other combinations of steps or compositions are included, even though not explicitly stated.

TABLE 1 hCG Dosing Strategy.

| Total Dose (IUs hCG) | Dose/injection (IUs hCG) | Dose/injection (micrograms (μg) hCG) |
|---|---|---|
| FIGS. 3 and 4 Dosed on days 1, 3, and 5 RSA (no stroke) RSA | | |
| 330 | 110 | 11 |
| 990 | 330 | 33 |
| 9900 | 3300 | 330 |
| 30000 | 10000 | 1000 |
| FIGS. 5 and 6 Dosed daily for 7 days Untreated (no stroke and no injections) RSA | | |
| 7000 | 1000 | 100 |
| 23100 | 3300 | 330 |
| 46200 | 6600 | 660 |
| 70000 | 10000 | 1000 |
| Dosed on days 1, 3, and 5 | | |
| 23100 | 7700 | 770 |

Rats received either three intramuscular (I.M.) injections of hCG over 5 days or daily injections or 7 days beginning 24 hrs post-stroke. Control rats received injections of RSA only.

TABLE 2

Actual values ± SEM presented as the average number of positive cells per lateral ventricle for quantification of pHH3+, BrdU+ and DCX+ cells in animals dosed with hCG 24 hrs following pial strip devascularizing stroke relative to controls.

| Dosing Condition (μg/injection) | pHH3+ Cells Number of Positive Cells per Ventricle | |
|---|---|---|
| | | BrdU+ Cells |
| Daily Dosing for 1 Week | | |
| Untreated No Stroke | 8.7 ± 2 | — |
| RSA | 9.3 ± 0.3 | 374 ± 15 |
| 10 | 19.3 ± 5 | 459 ± 138 |
| 330 | 27 ± 3** | 874 ± 91* |
| 660 | 12.3 ± 2 | — |
| 1000 | 17 ± 2 | — |
| 770 (dosed on days 1, 3 and 5) | 16 ± 1 | — |
| | | DCX+ Cells |
| 5 Day Dosing with Injections on Days 1, 3 and 5 | | |
| RSA | 8.7 ± 1 | 280 ± 15 |
| 11 | 8 ± 2 | — |
| 33 | 8 ± 0.1 | — |
| 330 | 13 ± 1 | — |
| 1000 | 19 ± 1* | 533 ± 42* |

What is claimed is:

1. A method for treating or ameliorating a central nervous system (CNS) injury in a mammal having or suspected of having a CNS injury, wherein the CNS injury is selected from stroke or ischemia, the method comprising administering an effective amount of a human chorionic gonadotropin (hCG) to the mammal, wherein the effective amount of the hCG increases the number of neural stem cells in the mammal, wherein the hCG is administered to the mammal during a first treating period, wherein the total dosage of the hCG administered in said first treating period of time equals the effective amount, and wherein said first treating period is at least three days.

2. The method of claim 1, wherein the duration of the first treating period is selected from the group consisting of at least four days, at least five days, at least six days, at least seven days, and at least fourteen days.

3. The method of claim 1, further comprising administering to the mammal a human chorionic gonadotropin (hCG) in a second treating period, wherein the second treating period starts after the end of the first treating period, and wherein the second treating period is at least three days.

4. The method of claim 1, wherein the hCG administered by systemic injection at least once per day.

5. The method of claim 1, wherein the hCG is not administered by infusion.

6. The method of claim 1, wherein the amount of hCG administered to the mammal is 0.5 IU/kg/day to about 3,000,000 IU/kg/day.

7. The method of claim 1, wherein the amount of hCG administered to the mammal is about 10,000 IU/day.

8. The method of claim 1, further comprising administering to the mammal a neural stem cell differentiating agent.

9. The method of claim 8, wherein the neural stem cell differentiating agent is an erythropoietin (EPO).

10. The method of claim 1, wherein the mammal is an adult.

11. The method of claim 1, wherein the ischemia is ocular isehemia.

12. The method of claim 1, wherein a first dose of the hCG is administered to the mammal within 14 days of an onset of symptoms or a diagnosis of the CNS injury.

13. The method of claim 1, wherein a first dose of the hCG is administered to the mammal within 5 days of an onset of symptoms or a diagnosis of the CNS injury.

* * * * *